(12) United States Patent
Bates et al.

(10) Patent No.: US 9,452,219 B2
(45) Date of Patent: Sep. 27, 2016

(54) ANTI-NUCLEOLIN AGENT-CONJUGATED NANOPARTICLES

(75) Inventors: Paula J. Bates, Louisville, KY (US); Mohammad Tariq Malik, Prospect, KY (US); Kyung A. Kang, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 157 days.

(21) Appl. No.: 14/122,617

(22) PCT Filed: Jun. 1, 2012

(86) PCT No.: PCT/US2012/040577
§ 371 (c)(1),
(2), (4) Date: Feb. 26, 2014

(87) PCT Pub. No.: WO2012/167173
PCT Pub. Date: Dec. 6, 2012

(65) Prior Publication Data
US 2014/0170076 A1 Jun. 19, 2014

Related U.S. Application Data

(60) Provisional application No. 61/492,683, filed on Jun. 2, 2011.

(51) Int. Cl.
| | | |
|---|---|---|
| *A61K 51/00* | (2006.01) | |
| *A61M 36/14* | (2006.01) | |
| *A61K 47/48* | (2006.01) | |
| *A61K 49/04* | (2006.01) | |

(52) U.S. Cl.
CPC ... *A61K 47/48015* (2013.01); *A61K 47/48169* (2013.01); *A61K 47/48238* (2013.01); *A61K 47/48884* (2013.01); *A61K 49/04* (2013.01); *Y10T 428/2982* (2015.01)

(58) Field of Classification Search
CPC .......... A61K 47/00; A61K 47/48169; A61K 47/48238; A61K 47/8884; A61K 49/04; A61K 47/48015; Y10T 428/2982
USPC .......... 424/1.11, 1.49, 1.65, 1.69, 1.73, 400, 424/489, 490; 977/773; 514/1, 1.1, 19.2, 514/19.3, 19.4, 19.5, 19.6
See application file for complete search history.

(56) References Cited

U.S. PATENT DOCUMENTS

| | | | |
|---|---|---|---|
| 4,474,892 A | 10/1984 | Murad et al. | |
| 4,522,811 A | 6/1985 | Eppstein et al. | |
| 4,665,897 A | 5/1987 | Lemelson | |
| 5,055,459 A | 10/1991 | Andersson et al. | |
| 5,093,246 A | 3/1992 | Cech et al. | |
| 5,192,660 A | 3/1993 | Reed-Gitomer | |
| 5,530,101 A | 6/1996 | Queen et al. | |
| 5,545,807 A | 8/1996 | Surani et al. | |
| 5,567,595 A | 10/1996 | Kok | |
| 5,629,197 A | 5/1997 | Ring et al. | |
| 5,736,348 A | 4/1998 | Goldenberg et al. | |
| 5,739,306 A | 4/1998 | Fung et al. | |
| 5,770,429 A | 6/1998 | Lonberg et al. | |
| 5,869,045 A | 2/1999 | Hellstrom et al. | |
| 5,925,334 A | 7/1999 | Rubin et al. | |
| 5,932,475 A | 8/1999 | Bandman et al. | |
| 6,048,703 A | 4/2000 | Siman et al. | |
| 6,096,532 A | 8/2000 | Armstrong et al. | |
| 6,165,786 A | 12/2000 | Bennett et al. | |
| 6,291,643 B1 | 9/2001 | Zou et al. | |
| 6,306,404 B1 | 10/2001 | LaPosta et al. | |
| 6,325,785 B1 | 12/2001 | Babkes et al. | |
| 6,339,075 B1 | 1/2002 | King et al. | |
| 6,350,452 B1 | 2/2002 | Riss | |
| 6,462,189 B1 | 10/2002 | Koide | |
| 6,506,559 B1 | 1/2003 | Fire et al. | |
| 6,657,103 B1 | 12/2003 | Kucherlapati et al. | |
| 7,259,252 B2 * | 8/2007 | Mirkin et al. | ............... 536/23.1 |
| 7,314,926 B1 * | 1/2008 | Miller et al. | ................. 536/24.1 |
| 7,357,928 B2 | 4/2008 | Bates et al. | |
| 7,541,150 B2 | 6/2009 | Miller et al. | |
| 8,029,784 B2 | 10/2011 | Bates et al. | |
| 8,586,717 B2 | 11/2013 | Bates et al. | |
| 2002/0028488 A1 | 3/2002 | Singh et al. | |
| 2002/0076693 A1 | 6/2002 | Hovanessian et al. | |
| 2003/0086930 A1 | 5/2003 | Mueller | |
| 2003/0194754 A1 | 10/2003 | Miller et al. | |
| 2004/0132049 A1 | 7/2004 | Bates et al. | |
| 2005/0026860 A1 | 2/2005 | Lin et al. | |

(Continued)

FOREIGN PATENT DOCUMENTS

| | | |
|---|---|---|
| AU | 762572 | 11/1999 |
| AU | 2003234694 | 3/2006 |

(Continued)

OTHER PUBLICATIONS

Waldmann, T.A., "Immunotherapy: past, present and future", Nature Medicine, vol. 9, No. 3, pp. 269-277, (2003).
44 Pages, May 20, 2015, U.S. Appl. No. 14/059,211.
5 Pages, Feb. 4, 2015, U.S. Appl. No. 14/059,211.
Malik, M.T. et al., "Aptamers conjugated to gold nanoparticles and their potential for breast cancer imaging and therapy", Research Louisville 2011, University of Louisville, Louisville, Kentucky (Finalist, Post-Doctoral Category), Abstract # PRF-52.
16 Pages, Nov. 25, 2008, U.S. Appl. No. 10/607,455.
17 Pages, Feb. 6, 2008, U.S. Appl. No. 10/607,455.
18 Pages, Aug. 9, 2007, U.S. Appl. No. 10/607,455.
7 Pages, Feb. 7, 2007, U.S. Appl. No. 10/607,455.
3 Pages, Nov. 6, 2006, U.S. Appl. No. 10/607,455.
13 Pages, Jul. 28, 2006, U.S. Appl. No. 10/607,455.
19 Pages, Nov. 23, 2005, U.S. Appl. No. 10/607,455.

(Continued)

*Primary Examiner* — D L Jones
(74) *Attorney, Agent, or Firm* — Evan Law Group LLC

(57) ABSTRACT

A composition comprises an anti-nucleolin agent conjugated to nanoparticles. The nanoparticles are non-magnetic, not iron oxide and not polyacrylamide. Furthermore, a pharmaceutical composition for treating cancer comprises a composition including an anti-nucleolin agent conjugated to nanoparticles, and a pharmaceutically acceptable carrier.

20 Claims, 14 Drawing Sheets

(56) References Cited

U.S. PATENT DOCUMENTS

| | | | |
|---|---|---|---|
| 2005/0053607 A1 | 3/2005 | Bates et al. | |
| 2005/0187176 A1 | 8/2005 | Bates et al. | |
| 2006/0258605 A1 | 11/2006 | Luo et al. | |
| 2009/0017009 A1 | 1/2009 | Bates et al. | |
| 2009/0226914 A1 | 9/2009 | Bates et al. | |
| 2011/0065121 A1 | 3/2011 | Bates et al. | |
| 2011/0091373 A1 | 4/2011 | Pandey et al. | |
| 2011/0111002 A1 | 5/2011 | Pop | |
| 2012/0014942 A1 | 1/2012 | Bates et al. | |
| 2013/0115674 A1* | 5/2013 | Sutkowski et al. | 435/188 |

FOREIGN PATENT DOCUMENTS

| | | |
|---|---|---|
| AU | 2003234694 | 4/2007 |
| AU | 2004279837 | 12/2007 |
| AU | 2003234694 | 5/2008 |
| AU | 2003248724 | 9/2008 |
| AU | 2004279837 | 6/2009 |
| AU | 2010202113 | 1/2012 |
| CA | 2490724 | 11/2004 |
| CA | 2490724 | 12/2009 |
| CA | 2489520 | 5/2010 |
| CA | 2490724 | 6/2010 |
| CA | 2490724 | 7/2010 |
| CA | 2489520 | 3/2011 |
| CA | 2546730 | 6/2011 |
| CA | 2546730 | 7/2012 |
| CA | 2 549 467 | 12/2012 |
| CA | 2546730 | 3/2013 |
| CA | 2 542 691 | 9/2013 |
| CA | 2 545 806 | 9/2014 |
| CA | 2546730 | 3/2015 |
| DE | 10037861 | 2/2002 |
| EP | 03 728 350.4 | 7/2005 |
| EP | 03 728 350.4 | 9/2005 |
| EP | 03 762 073.9 | 10/2006 |
| EP | 03 762 073.9 | 5/2007 |
| EP | 03 728 350.4 | 11/2007 |
| EP | 03 762 073.9 | 2/2008 |
| EP | 03 728 350.4 | 6/2008 |
| EP | 03 762 073.9 | 12/2008 |
| EP | 04 785 392.4 | 12/2008 |
| EP | 03 762 073.9 | 7/2009 |
| EP | 04 785 392.4 | 4/2010 |
| EP | 04 785 392.4 | 11/2011 |
| EP | 04 785 392.4 | 4/2013 |
| EP | 04 785 392.4 | 9/2013 |
| EP | 04 785 392.4 | 10/2013 |
| EP | 12730288.3 | 1/2014 |
| EP | 12730288.3 | 10/2014 |
| EP | 12730288.3 | 1/2015 |
| EP | 12730288.3 | 3/2015 |
| EP | 12730288.3 | 1/2016 |
| EP | 15182208.7 | 3/2016 |
| JP | 1-503438 | 11/1989 |
| JP | 5-244988 | 9/1993 |
| JP | 07 242566 A | 9/1995 |
| JP | 1995/242566 | 9/1995 |
| JP | 2001-213804 | 8/2001 |
| JP | 2003-583205 | 5/2009 |
| JP | 2006-534360 | 7/2009 |
| JP | 2004-517874 | 8/2009 |
| JP | 2003-583205 | 4/2010 |
| JP | 2006-534360 | 5/2010 |
| JP | 2003-583205 | 9/2010 |
| JP | 2011-127396 | 9/2011 |
| JP | 2011-127396 | 12/2011 |
| JP | 2011-127396 | 8/2012 |
| JP | 2012-266961 | 3/2014 |
| JP | 2012-266961 | 2/2015 |
| WO | WO 88/07543 | 10/1988 |
| WO | WO 95/20401 | 8/1995 |
| WO | WO 97/22250 | 6/1997 |
| WO | WO 98/24893 | 6/1998 |
| WO | WO 98/40480 | 9/1998 |
| WO | WO 99/06588 | 2/1999 |
| WO | WO 99/53057 | 10/1999 |
| WO | WO 00/61597 | 10/2000 |
| WO | WO 00/63250 | 10/2000 |
| WO | WO 01/32832 | 5/2001 |
| WO | WO 01/35093 | 5/2001 |
| WO | WO 01/68836 | 9/2001 |
| WO | WO 01/75164 | 10/2001 |
| WO | WO 01/91787 | 12/2001 |
| WO | WO 02/12437 | 2/2002 |
| WO | WO 02/44321 | 6/2002 |
| WO | WO 03/029277 | 4/2003 |
| WO | WO 03/008617 | 10/2003 |
| WO | WO 03/086174 | 10/2003 |
| WO | WO 03/087124 | 10/2003 |
| WO | PCT/US2003/020167 | 11/2003 |
| WO | WO 2004/003554 | 1/2004 |
| WO | PCT/US03/10745 | 8/2004 |
| WO | PCT/US2003/010745 | 8/2004 |
| WO | PCT/US2004/033174 | 3/2005 |
| WO | WO 2005/035579 | 4/2005 |
| WO | PCT/US2004/033174 | 4/2006 |
| WO | WO 2007/016466 | 2/2007 |
| WO | PCT/US2008/088491 | 7/2009 |
| WO | WO 2009/088837 | 7/2009 |
| WO | PCT/US2009/088491 | 9/2009 |
| WO | PCT/US2008/088491 | 7/2010 |
| WO | WO 2011/062997 | 5/2011 |
| WO | WO 2011/119058 | 9/2011 |
| WO | PCT/US2012/040577 | 9/2012 |
| WO | WO 2012/167173 | 12/2012 |
| WO | PCT/US2012/040577 | 12/2013 |

OTHER PUBLICATIONS

6 Pages, Jun. 29, 2005, U.S. Appl. No. 10/607,455.
5 Pages, Apr. 16, 2008, U.S. Appl. No. 10/118,854.
6 Pages, Sep. 19, 2007, U.S. Appl. No. 10/118,854.
7 Pages, Jan. 3, 2007, U.S. Appl. No. 10/118,854.
3 Pages, Oct. 17, 2006, U.S. Appl. No. 10/118,854.
2 Pages, Aug. 8, 2006, U.S. Appl. No. 10/118,854.
12 Pages, Mar. 31, 2006, U.S. Appl. No. 10/118,854.
3 Pages, Dec. 15, 2005, U.S. Appl. No. 10/118,854.
5 Pages, Jul. 26, 2005, U.S. Appl. No. 10/118,854.
14 Pages, Nov. 4, 2004, U.S. Appl. No. 10/118,854.
8 Pages, Jul. 1, 2004, U.S. Appl. No. 10/118,854.
3 Pages, Sep. 6, 2006, U.S. Appl. No. 10/118,854.
4 Pages, Oct. 25, 2007, U.S. Appl. No. 10/683,480.
6 Pages, Jun. 1, 2007, U.S. Appl. No. 10/683,480.
4 Pages, Nov. 27, 2006, U.S. Appl. No. 10/683,480.
2 Pages, Aug. 8, 2006, U.S. Appl. No. 10/683,480.
10 Pages, Jun. 5, 2006, U.S. Appl. No. 10/683,480.
10 Pages, Feb. 23, 2006, U.S. Appl. No. 10/683,480.
33 Pages, Nov. 13, 2009, U.S. Appl. No. 12/041,969.
10 Pages, Jun. 7, 2010, U.S. Appl. No. 12/041,969.
9 Pages, Sep. 28, 2010, U.S. Appl. No. 12/345,626.
3 Pages, Oct. 18, 2010, U.S. Appl. No. 12/041,969.
2 Pages, Feb. 1, 2010, U.S. Appl. No. 10/607,455.
2 Pages, Jun. 27, 2008, U.S. Appl. No. 10/607,455.
3 Pages, Sep. 18, 2006, U.S. Appl. No. 10/607,455.
9 Pages, Dec. 21, 2010, U.S. Appl. No. 12/604,212.
34 Pages, Mar. 30, 2011, U.S. Appl. No. 12/604,212.
4 Pages, Nov. 23, 2010, U.S. Appl. No. 12/041,969.
33 Pages, Dec. 27, 2010, U.S. Appl. No. 12/345,626.
33 Pages, Jan. 7, 2011, U.S. Appl. No. 12/345,626.
3 Pages, Jun. 15, 2011, U.S. Appl. No. 12/041,969.
6 Pages, Jun. 9, 2011, U.S. Appl. No. 12/041,969.
15 Pages, Jul. 28, 2011, U.S. Appl. No. 12/345,626.
14 Pages, Sep. 28, 2011, U.S. Appl. No. 12/604,212.
2 Pages, Jan. 26, 2012, U.S. Appl. No. 12/604,212.
34 Pages, Jul. 10, 2012, U.S. Appl. No. 13/116,319.
17 Pages, Feb. 26, 2013, U.S. Appl. No. 13/116,319.
3 Pages, Jun. 18, 2013, U.S. Appl. No. 13/116,319.
52 Pages, Jul. 15, 2013, U.S. Appl. No. 12/604,212.
7 Pages, Jul. 5, 2013, U.S. Appl. No. 13/116,319.

(56) References Cited

OTHER PUBLICATIONS

Abaza, M.S.I, et al, "Effects of amino acid substitutions outside an antigenic site on protein binding to monoclonal antibodies of predetermined specificity obtained by peptide immunization: Demonstration with region 94-100 (antigenic site 3) of myoglobin", Journal of Protein Chemistry, vol. 11, No. 5, pp. 433-444, (1992).
Agrawal, S, et al, "Antisense therapeutics: is it as simple as complementary base recognition?", Mol Med Today, vol. 6, No. 2, pp. 72-81, (2000).
Aihara, M, et al, "The frequency of apoptosis correlates with the prognosis of Gleason Grade 3 adenocarcinoma of the prostate", Cancer, vol. 75, No. 2, pp. 522-529, (1995).
Aihara, M, et al, "Frequency of apoptotic bodies positively correlates With Gleason grade in prostate cancer", Hum Pathol, vol. 25, No. 8, pp. 797-801, (1994).
Ali, S, et al, "Absorption, distribution, metabolism, and excretion of a respirable antisense oligonucleotide for asthma", Am J Respir Crit Care Med, vol. 163, No. 4, pp. 989-993, (2001).
Altman, S, "Nobel lecture. Enzymatic cleavage of RNA by RNA", Biosci Rep, vol. 10, No. 4, pp. 317-337, (1990).
Alvarex-Gonzalez, R, et al, "Selective loss of poly(ADP-ribose) and the 85-kDa fragment of ply(ADP-ribose) polymerase in nucleoli during alkylation-induced apoptosis of HeLa Cells", J Biol Chem., vol. 274, No. 45, pp. 32122-32126, (1999).
Anderson, H.J, et al, "Flow cytometry of mitotic cells", Exp Cell Research, vol. 238, No. 2, pp. 498-502, (1998).
Andrade, F, et al, "Apoptosis in systemtic lupus erythematosus", Rheumatic Diseases Clinics of North America, vol. 2, (2000).
Awang, G, et al, "Mode of dimerization of HIV-1 genomic RNA", Biochemistry, vol. 32, No. 42, pp. 11453-11457, (1993).
Ballou, B, et al, "Three-Dimensional Imaging of Nucleolin Trafficking in Normal Cells, Transfectants, and Heterokaryons", SPIE, vol. 2680, pp. 124-131, (1996).
Ballou, B, et al, "Tumor Detection and Visualization Using Cyanine Fluorochrome-Labeled Antibodies", Biotechnol Prog, vol. 13, pp. 649-658, (1997).
Ballou, B, et al, "Tumor Labeling in Vivo Using Cyanine-Conjugated Monoclonal Antibodies", Cancer Immunol Immunother, vol. 41, pp. 257-263, (1995).
Ballou, B, et al, Abstract of "Cyanine Fluorocrome-Labeled Antibodies In Vivo: Assessment of Tumor Imaging Using Cy3, Cy5, Cy5.5, and Cy7", Cancer Detect Prev, vol. 22, No. 3, pp. 251-257, (1998).
Baran, N, et al, "The SV40 large T-antigen helicase can unwind four stranded DNA structures linked by G-quartets", Nucleic Acids Research, vol. 25, No. 2, pp. 297-303, (1997).
Barton, C.M, et al, "Antisense oligonucleotides directed against p53 have antiproliferative effects unrelated to effects on p53 expression", Br J Cancer, vol. 71, No. 3, pp. 429-437, (1995).
Bates, P.J, et al, "Antiproliferative activity of G-rich oligonucleotides correlates with protein binding", The Journal of Biological Chemistry, vol. 274, No. 37, pp. 26369-26377, (1999).
Beedassy, A, et al, "Chemotherapy in advanced prostate cancer", Semin Oncol, vol. 26, No. 4, pp. 428-438, (1999).
Beltinger, C, et al, "Binding, uptake, and intracellular trafficking of phosphorothioate-modified oligodeoxynucleotides", J Clin Invest, vol. 95, No. 4, pp. 1814-1823, (1995).
Benimetskaya, L, et al, "Formation of a G-tetrad and higher order structures correlates with biological activity of the RelA (NF-kappaB p65) 'antisense' oligodeoxynucleotide", Nucleic Acids Research, vol. 25, No. 13, pp. 2648-2656, (1997).
Benton, B.M, et al, "A novel FK506- and rapamycin-binding protein (FPR3 gene product) in the yeast Saccharomyces cerevisiae is a praline rotamase localized to the nucleolus", J Cell Biol, vol. 127, No. 3, pp. 623-639, (1994).
Bergsmedh, A, et al, "Horizontal transfer of oncogenes by uptake of apoptotic bodies", Proc Natl Acad Science USA, vol. 98, No. 11, pp. 6407-6411, (2001).
Bergsmedh, A, et al, "Loss of the p21(Cip1/Waf1) cyclin kinase inhibitor results in propagation of horizontally transferred DNA", Cancer Research, vol. 62, No. 2, pp. 575-579, (2002).
Bernardi, F.D, et al, "A prognostic model of survival in surgically resected squamous cell carcinoma of the lung using clinical, pathologic, and biologic markers", Mod Pathol, vol. 10, No. 10, pp. 992-1000, (1997).
Bernstein, E, et al, "Role for a bidentate ribonuclease in the initiation step of RNA interference", Nature, vol. 409, No. 6818, pp. 363-366, (2001).
Bharti, A.K, et al, "Identification of a nucleolin binding site in human topoisomerase I", J Biol Chem, vol. 271, No. 4, pp. 1993-1997, (1996).
Biggiogera, M, et al, "Heterogeneous ectopic RNP-derived structures (HERDS) are markers of transcriptional arrest", FASEB J, vol. 14, No. 5, pp. 828-834, (2000).
Biscotti, C.V, et al, "Apoptotic bodies: a consistent morphologic feature of endocervical adenocarcinoma in situ", American Journal of Surgical Pathology, vol. 22, No. 4, pp. 434-439, (1998).
Bishop, J.S, et al, "Intramolecular G-quartet motifs confer nuclease resistance to a potent anti-HIV oligonucleotide", J Biol Chem, vol. 271, No. 10, pp. 5698-5703, (1996).
Blau, H.M, et al, "Tet B or not tet B: Advances in tetracycline-inducible gene expression", Proc Natl Acad Science USA, vol. 96, pp. 797-799, (1999).
Bock, L.C, et al, "Selection of single-stranded DNA molecules that bind and inhibit human thrombin", Nature, vol. 355, No. 6360, pp. 564-566, (1992).
Borer, R.A, et al, "Major nucleolar proteins shuttle between nucleus and cytoplasm", Cell, vol. 56, No. 3, pp. 379-390, (1989).
Borggrefe, T, et al, "A B-cell-specific DNA recombination complex", J Biol Chem, vol. 273, No. 27, pp. 17025-17035, (1998).
Borst, P, et al, "Does resistance to apoptosis affect clinical response to antitumor drugs?", Drug Resist Update, vol. 4, No. 2, pp. 129-131, (2001).
Bortul, R, et al, "Nuclear changes in necrotic HL-60 cells", J Cell Biochem, vol. 81, No. S36, pp. 19-31, (2001).
Boulares, A.H, et al, "Role of poly (ADP-ribose) polymerase (PARP) cleavage in apoptosis. Caspase 3-resistant PARP mutant increases rates of apoptosis in transfected cells", Journal of Biological Chemistry, vol. 274, No. 33, pp. 22932-22940, (1999).
Boulares, A.H, et al, "Roles of DNA fragmentation factor and poly(ADP-ribose) polymerase in an amplification phase of tumor necrosis factor-induced apoptosis", Journal of Biological Chemistry, vol. 276, No. 41, pp. 38185-38192, (2001).
Brockstedt, E, et al, "Identification of apoptosis-associated proteins in a human Burkitt lymphoma cell line. Cleavage of heterogeneous nuclear ribonucleoprotein A1 by caspase 3", J Biol Chem, vol. 273, No. 43, pp. 28057-28064, (1998).
Brown, J.M, et al, "Apoptosis: mediator or mode of cell killing by anticancer agents?", Drug Resist Update, vol. 4, No. 2, pp. 135-136, (2001).
Brustmann, H, "Apoptotic bodies as a morphological feature in serous ovarian carcinoma: correlation with nuclear grade, Ki-67 and mitotic indices", Pathol Res Pract, vol. 198, No. 2, pp. 85-90, (2002).
Burgess, T.L, et al, "The antiproliferative activity of c-myb and c-myc antisense oligonucleotides in smooth muscle cells is caused by a nonantisense mechanism", Proc Natl Acad Science USA, vol. 92, No. 9, pp. 4051-4055, (1995).
Buys, C.H, "Telomeres, telomerase, and cancer", N Engl J Med, vol. 342, No. 17, pp. 1282-1283, (2000).
Callebaut, C, et al, "Identification of V3 loop-binding proteins as potential receptors implicated in the binding of HIV particles to CD4(+) cells", J Biol Chem, vol. 273, No. 34, pp. 21988-21997, (1998).
Cannvo, G, et al, "Abnormal intracellular kinetics of cell-cycle-dependent proteins in lymphocytes from patients infected with human immunodeficiency virus: a novel biologic link between immune activation, accelerated t-cell turnover, and high levels of apoptosis", Blood, vol. 97, No. 6, pp. 1756-1764, (2001).

(56) References Cited

OTHER PUBLICATIONS

Carney, D.N, et al, "Establishment and identification of small cell lung cancer cell lines having classic and variant features", Cancer Research, vol. 45, pp. 2913-2923, (1985).
Carvalho, P.E, et al, "Useful prognostic panel markers to express the biological tumor status in resected lung adenocarcinomas", Jpn J Clin Oncol, vol. 30, No. 11, pp. 478-486, (2000).
Cech, T.R, "Biologic catalysis by RNA", Harvey Lect, vol. 82, pp. 123-144, (1988).
Chern, J.H, et al, "Usefulness of AgNOR score in differentiating benign from malignant pulmonary aspiration cytology", Acta Cytol, vol. 41, No. 2, pp. 393-398, (1997).
Choi, N.G, et al, "Apoptosis and nuclear shapes in benign prostate hyperplasia and prostate adenocarcinoma: comparison with and relation to Gleason score", Int J Urol, vol. 6, No. 1, pp. 13-18, (1999).
Cole, S.P, et al, "Antibody production by human X human hybridomas in serum-free medium", J Immunol Methods, vol. 78, No. 2, pp. 271-278, (1985).
Coligan, J.E. et al., "Production of Monoclonal Antibodies", Current Protocols in Immunology, vol. 1, pp. 2.5.1-2.6.7, Wiley, New York, (1991).
Coqueret, O, et al, "Functional interaction of STAT3 transcription factor with the cell cycle inhibitor $p21^{WAF1/CIP1/SDI1}$", J Biol Chem, vol. 275, No. 25, pp. 18794-18800, (2000).
Cowan, K.H, et al, "Dihydrofolate reductase gene amplification and possible rearrangement in estrogen-responsive methotrexate-resistant human breast cancer cells", J Biol Chem, vol. 257, No. 24, pp. 15079-15086, (1982).
Crooke, S., "Oligonucleotide therapeutics: a prospectus." Antisense Research and Development, vol. 3, No. 1, pp. 1-2, (1993).
Crooke, S, "Progress in antisense technology: the end of the beginning", Methods Enzymol, vol. 313, pp. 3-45, (1999).
D'Amours, D, et al, "Poly(ADP-ribosyl)ation reactions in the regulation of nuclear functions", Biochem J, vol. 342, pt. 2, pp. 249-268, (1999).
Dagle, J.M, et al, "Selective degradation of targeted mRNAs using partially modified oligonucleotides", Methods Enzymol, vol. 313, pp. 420-436, (1999).
Daniely, Y, et al, "Formation of a complex between nucleolin and replication protein A after cell stress prevents initiation of DNA replication", J Cell Biology, vol. 149, No. 4, pp. 799-810, (2000).
Dapic, V, et al, "Antiproliferative activity of G-Quartet-forming oligonucleotides with backbone and sugar modifications", Biochemistry, vol. 41, No. 11, pp. 3676-3685, (2002).
David, K, et al, "Initial characterization of the apoptosis-inducing receptor for natural human anti-neuroblastoma IgM", Med Pediatr Oncol, vol. 36, No. 1, pp. 251-257, (2001).
David-Pfeuty, T, "Potent inhibitors of cyclin-dependent kinase 2 induce nuclear accumulation of wild-type p53 and nucleolar fragmentation in human untransformed and tumor-derived cells", Oncogene, vol. 18, No. 52, pp. 7409-7422, (1999).
Davis, K.A, et al, "Staining of cell surface human CD4 with 2'-F-pyrimidine-containing RNA aptamers for flow cytometry", Nucleic Acids Research, vol. 26, pp. 3915-3924, (1998).
De Jong, J.S, et al, "Number of apoptotic cells as a prognostic marker in invasive breast cancer", Br J Cancer, vol. 82, No. 2, pp. 368-373, (2000).
Dempsey, L.A, et al, "A specific isoform of hnRNP D interacts with DNA in the LR1 heterodimer: canonical RNA binding motifs in a sequence-specific duplex DNA binding protein", J Biol Chem, vol. 273, No. 44, pp. 29224-29229, (1998).
Dempsey, L.A, et al, "G4 DNA binding by LR1 and its subunits, nucleolin and hnRNP D, a role for G-G pairing in immunoglobulin switch recombination", J Biol Chem, vol. 274, No. 2, pp. 1066-1071, (1999).
Deng, J.S, et al, "Internalization of anti-nucleolin antibody into viable HEp-2 cells", Mol Biol Rep, vol. 23, No. 3-4, pp. 191-195, (1996).
Derenzini, M. "The AgNORs", Micron, vol. 31, No. 2, pp. 117-120, (2000).
Derenzini, M, et al, "The quantity of nucleolar proteins nucleolin and protein B23 is related to cell doubling time in human cancer cells", Lab Invest, vol. 73, No. 4, pp. 497-502, (1995).
Desnoyers, S, et al, "Alteration of the nucleolar localization of poly(ADP-ribose) polymerase upon treatment with transcription inhibitors", Exp Cell Research, vol. 227, No. 1, pp. 146-153, (1996).
Dickinson, L.A, et al, "Nucleolin is a matrix attachment region DNA-binding protein that specifically recognizes a region with high base-unpairing potential", Mol Cell Biology, vol. 15, No. 1, pp. 456-465, (1995).
Dranovsky, A, et al, "Cdc2 phosphorylation of nucleolin demarcates mitotic stages and alzheimer's disease pathology", Neurobiol Aging, vol. 22, No. 4, pp. 517-528, (2001).
Drews, J, "Drug discovery: a historical perspective", Science, vol. 287, No. 5460, pp. 1960-1964, (2000).
Drews J, et al, "Classic drug targets (special pull-out)", Nature Biotechnology, vol. 15, (1997).
Dryden, S, et al, "The lack of specificity of neuropeptide Y (NPY) antisense oligodeoxynucleotides administered intracerebroventricularly in inhibiting food intake and NPY gene expression in the rat hypothalamus", J Endocrinol, vol. 157, No. 1, pp. 169-175, (1998).
Dumler, I, et al, "Urokinase-induced mitogenesis is mediated by casein kinase 2 and nucleolin", Curr Biol, vol. 9, No. 24, pp. 1468-1476, (1999).
Dundr, M, et al, "The dynamics of postmitotic reassembly of the nucleolus", J Cell Biol, vol. 150, No. 3, pp. 433-446, (2000).
Edwards, T.K, et al, "Role for nucleolin/Nsr1 in the cellular localization of topoisomerase I", J Biol Chem, vol. 275, No. 46, pp. 36181-36188, (2000).
Eguchi, K, "Apoptosis in autoimmune diseases", Intern Med, vol. 40, No. 4, pp. 275-284, (2001).
Erard, M.S, et al, "A major nucleolar protein, nucleolin, induces chromatin decondensation by binding to histone H1", Eur J Biochem, vol. 175, No. 3, pp. 525-530, (1988).
European Search Report for Application No. 03728350.4 dated Jul. 12, 2005.
Facompre, M, et al, "Apoptotic response of HL-60 human leukemia cells to the antitumor drug NB-506, a glycosylated indolocarbazole inhibitor of topoisomerase 1", Biochem Pharmacol, vol. 61, No. 3, pp. 299-310, (2001).
Feltzer, R.E, et al, "Alkaline proteinase inhibitor of Pseudomonas aeruginosa. Interaction of native and N-terminally truncated inhibitor proteins with Pseudomonas metalloproteinases", J Biol Chem, vol. 275, No. 28, pp. 21002-21009, (2000).
Fielding, P, et al, "Heterogeneous nuclear ribonucleoprotein A2/B1 up-regulation in bronchial lavage specimens: a clinical marker of early lung cancer detection", Clincal Cancer Research, vol. 5, No. 12, pp. 4048-4052, (1999).
Fry, M, et al, "Human Werner syndrome DNA helicase unwinds tetrahelical structures of the fragile X syndrome repeat sequence d(CGG)n", J Biol Chem, vol. 274, No. 18, pp. 12797-12802, (1999).
Fry, M, et al, "The fragile X syndrome d(CGG)n nucleotide repeats form a stable tetrahelical structure", Proc Natl Acad Science USA, vol. 91, No. 11, pp. 4950-4954, (1994).
Gascoyne, R.D, et al, "Prognostic significance of Bcl-2 protein expression and Bcl-2 gene rearrangement in diffuse aggressive non-Hodgkin's lymphoma", Blood, vol. 90, No. 1, pp. 244-251, (1997).
Gautier, F, et al, "Identification of an apoptotic cleavage product of BARD1 as an autoantigen: a potential factor in the antitumoral response mediated by apoptotic bodies", Cancer Research, vol. 60, No. 24, pp. 6895-6900, (2000).
Gautier, F, et al, "Production and characterisation of a monoclonal antibody specific for apoptotic bodies derived from several tumour cell lines", Journal of Immunological Methods, vol. 228, pp. 49-58, (1999).
Gavrieli, Y, et al, "Identification of programmed cell death in situ via specific labeling of nuclear DNA fragmentation", The Journal of Cell Biology, vol. 119, No. 3, pp. 493-501, (1992).

(56) References Cited

OTHER PUBLICATIONS

Gey, G, et al, "Tissue culture studies of the proliferative capacity of cervical carcinoma and normal epithelium", Cancer Research, vol. 12, pp. 264, (1952).

Ghosh, M, et al, "Apoptosis in squamous cell carcinoma of the lung: correlation with survival and clinicopathological features", J Clin Pathol, vol. 54, No. 2, pp. 111-115, (2001).

Giaccone, G, et al, "Neuromedin B is present in lung cancer cell lines", Cancer Research, vol. 52, pp. 2732s-2736s, (1992).

Gibbs, J.B, "Mechanism-based target identification and drug discovery in cancer research", Science, vol. 287, No. 5460, pp. 1969-1973, (2000).

Gil, D, et al, "Intracellular redistribution of nucleolin upon interaction with the CD3epsilon chain of the T cell receptor complex", J Biol Chem, vol. 276, No. 14, pp. 11174-11179, (2001).

Giles, R.V, et al, "Selecting optimal oligonucleotide composition for maximal antisense effect following streptolysin O-mediated delivery into human leukaemia cells", Nucleic Acids Research, vol. 26, No. 7, pp. 1567-1575, (1998).

Gilloteaux, J. et al., "Cancer cell necrosis by autoschizis: synergism of antitumor activity of vitamin C: vitamin K3 on human bladder carcinoma T24 cells", Scanning, vol. 20, No. 8, pp. 564-575, (1998).

Ginisty, H, et al, "Structure and functions of nucleolin", J Cell Science, vol. 112, Pt. 6, pp. 761-772, (1999).

Giovannangeli, C. et al, "Progress in developments of triplex-based strategies", Antisense & Nucleic Acid Drug Development, vol. 7, No. 4, pp. 413-421, (1997).

Giraldo, R, et al, "The yeast telomere-binding protein RAP1 binds to and promotes the formation of DNA quadruplexes in telomeric DNA", EMBO J, vol. 13, No. 10, pp. 2411-2420, (1994).

Green, D. W, et al, "Beta-catenin antisense treatment decreases beta-catenin expression and tumor growth rate in colon carcinoma xenografts", J Surg Res, vol. 101, No. 1, pp. 16-20, (2001).

Grinstein, E, et al, "Nucleolin as Activator of Human Papillomavirus Type 18 Oncogene Transcription in Cervical Cancer", J Exp Med, vol. 196, No. 8, pp. 1067-1078, The Rockefeller University Press, (2002).

Gudas, J.M, et al, "Drug-resistant breast cancer cells frequently retain expression of a functional wild-type p53 protein", Carcinogenesis, vol. 17, No. 7, pp. 1417-1427, (1996).

Haese, A, "Serum markers for early detection and staging of prostate cancer, status report on current and future markers", Urologe A, vol. 42, No. 9, pp. 1172-1187, (2003).—(Abstract Only).

Halicka, H.D, et al, "Segregation of RNA and separate packaging of DNA and RNA in apoptotic bodies during apoptosis", Exp Cell Research, vol. 260, No. 2, pp. 248-256, (2000).

Hanahan, D, et al, "The hallmarks of cancer", Cell, vol. 100, No. 1, pp. 57-70, (2000).

Hanakahi, L.A, et al, "High affinity interactions of nucleolin with G-G-paired rDNA", J Biol Chem, vol. 274, No. 22, pp. 15908-15912, (1999).

Hanakahi, L.A, et al, "Nucleolin is one component of the B cell-specific transcription factor and switch region binding protein, LR1", Proc Natl Acad Science USA, vol. 94, No. 8, pp. 3605-3610, (1997).

Harms, G, et al, "Identification of nucleolin as a new L-selectin ligand", Biochem J, vol. 360, pp. 531-538, (2001).

Herceg, Z, et al, "Failure of poly(ADP-ribose) polymerase cleavage by caspases leads to induction of necrosis and enhanced apoptosis", Mol Cell Biol, vol. 19, No. 7, pp. 5124-5133, (1999).

Hirata, D, et al, "Nucleolin as the earliest target molecule of autoantibodies produced in MRL/lpr lupus-prone mice", Clin Immunol, vol. 97, No. 1, pp. 50-58, (2000).

Hirsch, F.R, et al, "Early detection of lung cancer: clinical perspectives of recent advances in biology and radiology", Clinical Cancer Research, vol. 7, No. 1, pp. 5-22, (2001).

Holdenrieder, S, et al, "Nucleosomes in serum as a marker for cell death", Clin Chem Lab Med, vol. 39, No. 7, pp. 596-605, (2001).

Holdenrieder, S, et al, "Nucleosomes in serum of patients with benign and malignant diseases", Int. J. Cancer, vol. 95, pp. 114-120, (2001).

Holdenrieder, S, et al, "Circulating nucleosomes in serum", Annals New York Academy of Sciences, vol. 945, pp. 93-102, (2001).

Holdenrieder, S, et al, "Quantification of nucleosomes in serum by the cell death detection ELISAplus", Biochemica, No. 1, pp. 25-27, (2002), (http://www.roche-applied-science.com/biochemica/no1_02/PDF/p25.pdf).

Holmgren, L, et al, "Horizontal transfer of DNA by the uptake of apoptotic bodies", Blood, vol. 93, No. 11, pp. 3956-3963, (1999).

Horky, M, et al, "Segregation of nucleolar components coincides with caspase-3 activation in cisplatin-treated HeLa cells", J Cell Science, vol. 114, pt. 4, pp. 663-670, (2001).

Hovanessian, A.G, et al, "The cell-surface-expressed nucleolin is associated with the actin cytoskeleton", Experimental Cell Research, vol. 261, pp. 312-328, (2000).

Huang, Z, "Bcl-2 family proteins as targets for anticancer drug design", Oncogene, vol. 19, No. 56, pp. 6627-6631, (2000).

Iida, A, et al, "Inducible gene expression by retrovirus-mediated transfer of a modified tetracycline-regulated system", J Virol, vol. 70, No. 9, pp. 6054-6059, (1996).

International Search Report dated Nov. 13, 2003 for PCT application No. PCT/US03/20167.

International Search Report dated Aug. 3, 2004 for PCT application No. PCT/US03/10745.

International Search Report dated Mar. 14, 2005 for PCT application No. PCT/US04/033174.

Irving, R.A, et al, "Ribosome display and affinity maturation: from antibodies to single v-domains and steps towards cancer therapeutics", J Immunol Methods, vol. 248, issues 1-2, pp. 31-45, (2001).

Ishikawa, F, et al, "Nuclear proteins that bind the pre-mRNA 3' splice site sequence r(UUAG/G) and the human telomeric DNA sequence d(TTAGGG)n", Mol Cell Biology, vol. 13, No. 7, pp. 4301-4310, (1993).

Jordan, P, et al, "Major cell surface-located protein substrates of an ecto-protein kinase are homologs of known nuclear proteins", Biochemistry, vol. 33, No. 49, pp. 14696-14706, (1994).

Jungblut, P.R, et al, "Proteomics in human disease: cancer, heart and infectious diseases", Electrophoresis, vol. 20, No. 10, pp. 2100-2110, (1999).

Kamma, H, et al, "Interaction of hnRNP A2/B1 isoforms with telomeric ssDNA and the in vitro function", Biochem Biophys Res Commun, vol. 280, No. 3, pp. 625-630, (2001).

Kaneko, S, et al, "Nucleolar organizer regions as a prognostic indicator for stage I non-small cell lung cancer", Cancer Research, vol. 51, No. 15, pp. 4008-4011, (1991).

Kennedy, T.C, et al, "Screening for lung cancer revisited and the role of sputum cytology and fluorescence bronchoscopy in a high-risk group", Chest, vol. 117, supplemental 4, pp. 72S-79S, (2000).

Keough, T, et al, "A method for high-sensitivity peptide sequencing using postsource decay matrix-assisted laser desorption ionization mass spectrometry", Proc Natl Acad Science USA, vol. 96, No. 13, pp. 7131-7136, (1999).

Kerr, J.F, et al, "Apoptosis: a basic biological phenomenon with wide-ranging implications in tissue kinetics", Br J Cancer, vol. 26, pp. 239-257, (1972).

Ketting, R.F, et al, "Dicer functions in RNA interference and in synthesis of small RNA involved in developmental timing in C elegans", Genes Dev, vol. 15, No. 20, pp. 2654-2659, (2001).

Kibbey, M.C, et al, "A 110-kD nuclear shuttling protein, nucleolin, binds to the neurite-promoting IKVAV site of laminin-1", J Neurosci Research, vol. 42, No. 3, pp. 314-322, (1995).

Kim, C.S, et al, "A micro double capillary method for rheologic measurements of lower airway secretions", Bull Eur Physiopathol Respir, vol. 18, pp. 915-927, (1982).

Knorre, D.G. et al., "Antisense oligonucleotide derivatives as gene-targeted drugs", Biomed Sci, vol. 1, No. 4, pp. 334-343, (1990).

Kohler, G, et al, "Continuous cultures of fused cells secreting antibody of predefined specificity", Nature, vol. 256, pp. 495-497, (1975).

Kohler, P.O, "Isolation, cloning, and hybridization of endocrine cell lines", Methods Enzymol, vol. 39, pp. 109-128, (1975).

(56) References Cited

OTHER PUBLICATIONS

Krantz, S, et al, "Purification and partial amino acid sequencing of a fructosyllysine-specific binding protein from cell membranes of the monocyte-like cell line U937", Biochim Biophys Acta, vol. 1266, No. 1, pp. 109-112, (1995).

Kuby, J, "Antigens", Immunology, Second Edition, chapter 4, pp. 85-96, W.H. Freeman and Company, New York, (1994).

Kumar, R.K, et al, "Improved double immunofluorescence for confocal laser scanning microscopy", J Histochem Cytochem, vol. 47, No. 9, pp. 1213-1218, (1999).

Kwiatkowski, B.A, et al, "Identification and cloning of a novel chromatin-associated protein partner of Epstein-Barr nuclear protein 2", Experimental Cell Research, vol. 300, pp. 223-233, (2004).

Lakka, S.S, et al, "Adenovirus-mediated antisense urokinase-type plasminogen activator receptor gene transfer reduces tumor cell invasion and metastasis in non-small cell lung cancer cell lines", Clinical Cancer Research, vol. 7, No. 4, pp. 1087-1093, (2001).

Langer, P.R, et al, "Enzymatic synthesis of biotin-labeled polynucleotides: novel nucleic acid affinity probes", Proc Natl Acad Sci USA, vol. 78, pp. 6633-6637, (1981).

Larrucea, S, et. al, "Internalization of factor J and cellular signalization after factor J-cell interaction", Biochem Biophys Res Commun, vol. 266, No. 1, pp. 51-57, (1999).

Larrucea, S, et al, "Cellular adhesion mediated by factor J, a complement inhibitor. Evidence for nucleolin involvement", J Biol Chem, vol. 273, No. 48, pp. 31718-31725, (1998).

Lau, Q.C, et al, "In vivo pro-apoptotic and antitumor efficacy of a c-Raf antisense phosphorothioate oligonucleotide: relationship to tumor size", Antisense Nucleic Acid Drug Development, vol. 12, No. 1, pp. 11-20, (2002).

Lebedeva, I, et al, "Antisense oligonucleotides: promise and reality", Annu Rev Pharmacol Toxicol, vol. 41, pp. 403-419, (2001).

Leitinger, N, et al, "ADP-ribosylation of nucleolar proteins in HeLa tumor cells", J Cell Biochem, vol. 52, No. 2, pp. 153-158, (1993).

Lichtenstein, A.V, et al, "Circulating nucleic acids and apoptosis", Annuals New York Academy of Sciences, vol. 945, pp. 239-249, (2001).

Lin, D.L, et al, "p53 is a mediator for radiation-repressed human TR2 orphan receptor expression in MCF-7 cells, a new pathway from tumor suppressor to member of the steroid receptor superfamily", J Biol Chem, vol. 271, pp. 14649-14652, (1996).

Lin, S, et al, "The biochemical status of the DNA synthesome can distinguish between permanent and temporary cell growth arrest", Cell Growth Differ, vol. 8, No. 12, pp. 1359-1369, (1997).

Little, C.D, et al, "Amplification and expression of the c-myc oncogene in human lung cancer cell lines", Nature, vol. 306, pp. 194-196, (1983).

Liu, H, et al, "Construction of a GAL1-regulated yeast cDNA expression library and its application to the identification of genes whose overexpression causes lethality in yeast", Genetics, vol. 132, No. 3, pp. 665-673, (1992).

Lopes de Menezes, D, et al, "Pharmacokinetics of Bcl-2 antisense oligonucleotide (G3139) combined with doxorubicin in SCID mice bearing human breast cancer solid tumor xenografts", Cancer Chemother Pharmacol, vol. 49, No. 1, pp. 57-68, (2002).

Lovborg, H, et al, "Modulation of pyridyl cyanoguanidine (CHS 828) induced cytotoxicity by 3-aminobenzamide in U-937 GTB cells", Biochem Pharmacol, vol. 63, No. 8, pp. 1491-1498, (2002).

Ma J, et al, "Cells designed to deliver anticancer drugs by apoptosis", Cancer Research, vol. 62, No. 5, pp. 1382-1387, (2002).

Mann, M, et al, "Analysis of proteins and proteomes by mass spectrometry", Annu Rev Biochem, vol. 70, pp. 437-473, (2001).

Martelli, A.M, et al, "Biochemical and Morphological characterization of the nuclear matrix from apoptotic HL-60 Cells", Journal of Cellular Biochemistry, vol. 72, No. 1, pp. 35-46, (1999).

Martelli, A.M, et al, "Behavior of nucleolar proteins during the course of apoptosis in camptothecintreated HL60 cells", Journal of Cellular Biochemistry, vol. 78, No. 2, pp. 264-277, (2000).

Martelli, A.M, et al, "Nuclear apoptotic changes: an overview", J Cell Biochem, vol. 82, No. 4, pp. 634-646, (2001).

Martin, S.J, et al, "Protease activation during apoptosis: death by a thousand cuts?" Cell, vol. 82, pp. 349-352, (1995).

Matthews, D.A, "Adenovirus protein V induces redistribution of nucleolin and B23 from nucleolus to cytoplasm", J Virol, vol. 75, No. 2, pp. 1031-1038, (2001).

Mattson, M.P., "Apoptosis in neurodegenerative disorders", Nature Reviews Mol Cell Biology, vol. 1, No. 2, pp. 120-129, (2000).

Mayer, T.U, et al, "Small molecule inhibitor of mitotic spindle bipolarity identified in a phenotype-based screen", Science, vol. 286, No. 5441, pp. 971-974, (1999).

McEwen, C.N, et al, "Negative gold ion gun for liquid secondary ion mass spectrometry", Anal Chem, vol. 57, No. 4, pp. 890-892, (1985).

McManus, M.T, et al, "Gene silencing in mammals by small interfering RNAs." Nat Rev Genet, vol. 3, No. 10, pp. 737-747, (2002).

McManus, M.T, et al, "Gene silencing using micro-RNA designed hairpins", RNA, vol. 8, No. 6, pp. 842-850, (2002).

McNicol, A.M, et al, "Optimizing immunohistochemistry: antigen retrieval and signal amplification", Histopathology, vol. 32, pp. 97-103, (1998).

Mehes, G, et al, "Nucleolin and fibrillarin expression in stimulated lymphocytes and differentiating HL-60 cells. A flow cytometric assay", Cell Prolif, vol. 28, No. 6, pp. 329-336, (1995).

Mi, Y, et al, "Validation of Nucleolin as a Novel Target for Cancer Drug Discovery", Proceedings of the American Association for Cancer Research Annual Meeting, vol. 43, Mar. 2002, pp. 959-960, $93^{rd}$ Annual Meeting of the American Association for Cancer Research, San Francisco, California, USA, Apr. 6-10, 2002.

Mickey, D.D, et al, "Heterotransplantation of a human prostatic adenocarcinoma cell line in nude mice", Cancer Research, vol. 37, pp. 4049-4058, (1977).

Mikolajczyk, S, et al, "Tumor-associated forms of prostate specific antigen improve the discrimination of prostate cancer from benign disease", Rinsho Byori, vol. 52, No. 3, pp. 223-230, (2004).

Minota, S, et al, "Autoantibodies to nucleolin in systemic lupus erythematosus and other diseases", J Immunol, vol. 146, No. 7, pp. 2249-2252, (1991).

Miranda, G.A, et al, "The murine nucleolin protein is an inducible DNA and ATP binding protein which is readily detected in nuclear extracts of lipopolysaccharide-treated splenocytes", Exp Cell Research, vol. 217, No. 2, pp. 294-308, (1995).

Morgan, D.M, "Tetrazolium (MTT) assay for cellular viability and activity", Meth Mol Biol, vol. 79, pp. 179-183, (1998).

Morimoto, Y, et al, "Alteration of argyrophilic nucleolar organizer region associated (Ag-NOR) proteins in apoptosis-induced human salivary gland cells and human oral aquamous carcinoma cells", J Oral Pathol Med, vol. 30, No. 4, pp. 193-199, (2001).

Morimoto, Y, et al, "Upregulation of the expression of Fas antigen and Fas ligand in a Human submandibular gland ductal cell line by okadaic acid", Arch Oral Biol, vol. 45, No. 8, pp. 657-666, (2000).

Morrison, S.L. et al, "Chimeric human antibody molecules: mouse antigen-binding domains with human constant region domains", Proceedings of the National Academy of Science USA, vol. 81, No. 21, pp. 6851-6855, (1984).

Murchie, A.I, et al, "Retinoblastoma susceptibility genes contain 5' sequences with a high propensity to form guanine-tetrad structures", Nucleic Acids Research, vol. 20, No. 1, pp. 49-53, (1992).

Naito, M, et al, "ATP/$Mg^{2+}$-dependent binding of vincristine to the plasma membrane of multifrug-resistant K562 cells", J Biol Chem, vol. 263, pp. 11887-11891, (1988).

Nakanishi, K, et al, "Argyrophilic nucleolar-organizer region counts and DNA status in bronchioloalveolar epithelial hyperplasia and adenocarcinoma of the lung", Hum Pathol, vol. 29, No. 3, pp. 235-239, (1998).

Navenot, J.M, et al, "Molecular anatomy of CCR5 engagement by physiologic and viral chemokines and HIV-1 envelope glycoproteins: differences in primary structural requirements for RANTES, MIP-1 alpha, and vMIP-II Binding", J Mol Biol, vol. 313, No. 5, pp. 1181-1193, (2001).

Neuberger, M.S, et al, "Recombinant antibodies possessing novel effector functions", Nature, vol. 312, No. 5995, pp. 604-608, (1984).

(56) References Cited

OTHER PUBLICATIONS

Nichols, R.C, et al, "The RGG domain in hnRNP A2 affects subcellular localization", Exp Cell Research, vol. 256, No. 2, pp. 522-532, (2000).

Nonomura, A, et al, "Demonstration of nucleolar organizer regions in lung carcinoma by silver staining", Surgery Today, vol. 23, pp. 486-490, (1993).

Norgaard, J.M, et al, "FAB M4 and high CD14 surface expression is associated with high cellular resistance to Ara-C and daunorubicin: implications for clinical outcome in acute myeloid leukaemia", European Journal of Haematology, vol. 67, pp. 221-229, (2001).

Nosseri, C, et al, "Possible involvement of poly(ADP-ribosyl) polymerase in triggering stress-induced apoptosis", Exp Cell Research, vol. 212, No. 2, pp. 367-373, (1994).

Ohkoudo, M, et al, "Morphometrical analysis of nucleolin immunohistochemistry in meningiomas", Acta Neuropathol, vol. 92, pp. 1-7, (1996).

Orfao, A, et al, "General concepts about cell sorting techniques", Clin Biochem, vol. 29, pp. 5-9, (1996).

Oyama, T, et al, "Nucleolar organizer regions are independently associated with a shortened survival in patients with non-small cell lung cancer", Surg Oncol, vol. 2, No. 6, pp. 341-347, (1993).

Paddison, P.J, et al, "Short hairpin RNAs (shRNAs) induce sequence-specific silencing in mammalian cells", Genes Dev, vol. 16, No. 8, pp. 948-958, (2002).

Paddison, P.J, et al, "Stable suppression of gene expression by RNAi in mammalian cells", Proc Natl Acad Science USA, vol. 99, No. 3, pp. 1443-1448, (2002).

Palomba, L, et al, "Apoptosis and necrosis following exposure of U937 cells to increasing concentrations of hydrogen peroxide: the effect of the poly(ADP-ribose) polymerase inhibitor 3-aminobenzamide", Biochem Pharmacol, vol. 58, No. 11, pp. 1743-1750, (1999).

Pandey, A, et al, "Proteomics to study genes and genomes", Nature, vol. 405, No. 6788, pp. 837-846, (2000).

Partridge, M. et al., "A simple method for delivering morpholino antisense oligos into the cytoplasm of cells", Antisense Nucleic Acid Drug Development, vol. 6, No. 3, pp. 169-175, (1996).

Pasternack, M.S, et al, "Granzyme A binding to target cell proteins Granzyme A binds to and cleaves nucleolin in vitro", J Biol Chem, vol. 266, No. 22, pp. 14703-14708, (1991).

Perry, S.W, et al, "Simultaneous in situ detection of apoptosis and necrosis in monolayer cultures by TUNEL and trypan blue staining", Biotechniques, vol. 22, No. 6, pp. 1102-1106, (1997).

Pich, A, et al, "Prognostic relevance of AgNORs in tumor pathology", Micron, vol. 31, No. 2, pp. 133-141, (2000).

Pinton, P, et al, "The $Ca^{2+}$ concentration of the endoplasmic reticulum is a key determinant of ceramide-induced apoptosis: significance for the molecular mechanism of Bcl-2 action", EMBO J, vol. 20, pp. 2690-2701, (2001).

Platt, N, et al, "Recognizing death: the phagocytosis of apoptotic cells", Trends Cell Biology, vol. 8, No. 9, pp. 365-372, (1998).

Pleschke, J.M, et al, "Poly(ADP-ribose) binds to specific domains in DNA damage checkpoint proteins", J Biol Chem, vol. 275, No. 52, pp. 40974-40980, (2000).

Product Data Sheet for ab7898 from http://www.abcam.com/?datasheet=7898, (1998-2006).

Product Data Sheet for C23 (C-18): sc-9892, Santa Cruz Biotechnology, Inc, (2003).

Product Data Sheet for C23 (MS-3): sc-8031, Santa Cruz Biotechnology, Inc, (2004).

Product Data Sheet for C23 (F-18): sc-9893, Santa Cruz Biotechnology, Inc, (2003).

Product Data Sheet for p7-1A4, from http://dshb.biology.uiowa.edu/objects/catalog//product/extras/4217_p7-1A4.pdf, Antibody Database Information, printed on Aug. 10, 2007.

Product Data Sheet for B23 (C-19): sc-6013, Santa Cruz Biotechnology, Inc., located at http://datasheets.scbt.com/sc-6013.pdf, printed on Aug. 10, 2007.

Product Data Sheet for B23 (H-106): sc-5564, Santa Cruz Biotechnology, Inc., located at http://datasheets.scbt.com/sc-5564.pdf, printed on Aug. 10, 2007.

Product Data Sheet for Monoclonal Antibody, Anti-Nucleolin M019-3, Medical & Biological Laboratories Co, LTD, www.mblintl.com, (2003).

Product Data Sheet for Anti-Nucleolin, Clone 3G4B2, Upstate Biotechnology, http://www.upstate.com/browse/productdetail.asp?ProductId=05-565, (2005).

Puttaraju, M, et al, "Messenger RNA repair and restoration of protein function by spliceosome-mediated RNA trans-splicing", Mol Ther, vol. 4, No. 2, pp. 105-114, (2001).

Raab de Verdugo, U, et al, "Characterization of a 100-kilodalton binding protein for the six serotypes of coxsackie B viruses", Journal of Virology, vol. 69, No. 11, pp. 6751-6757, (1995).

Richardson, D.S, et al, "Effects of PARP inhibition on drug and Fas-induced apoptosis in leukaemic cells", Adv Exp Med Biol, vol. 457, pp. 267-279, (1999).

Robinson, J.M, et al, "Antigen retrieval in cells and tissues: enhancement with sodium dodecyl sulfate", Histochem Cell Biol, vol. 116, pp. 119-130, (2001).

Roninson, I.B, et al, "If not apoptosis, then what? Treatment-induced senescence and mitotic catastrophe in tumor cells", Drug Resist Update, vol. 4, No. 5, pp. 303-313, (2001).

Rosenthal, D.S, et al, "Detection of DNA breaks in apoptotic cells utilizing the DNA binding domain of poly(ADP-ribose) Polymerase with fluorescence microscopy", Nucleic Acids Research, vol. 25, No. 7, pp. 1437-1441, (1997).

Rothenburg, S, et al, "A polymorphic dinucleotide repeat in the rat nucleolin gene forms Z-DNA and inhibits promoter activity", PNAS, vol. 98, No. 16, pp. 8985-8990, (2001).

Roussel, P, et al, "Identification of Ag-NOR proteins, markers of proliferation related to ribosomal gene activity", Experimental Cell Research, vol. 214, No. 2, pp. 465-472, (1994).

Roussel, P, et al, "Quantification of Ag-NOR proteins using Ag-NOR staining on western blots", Histochem Cytochem, vol. 42, No. 11, pp. 1513-1517, (1994).

Saijo, Y, et al, "Contiguous four-guanosine sequence in c-myc antisense phosphorothioate oligonucleotides inhibits cell growth on human lung cancer cells: possible involvement of cell adhesion inhibition", Jpn J Cancer Research, vol. 88, No. 1, pp. 26-33, (1997).

Saikumar, P, et al, "Apoptosis: definition, mechanisms, and relevance to disease", Am J Med, vol. 107, No. 5, pp. 489-506, (1999).

Sandoval, A, et al, "Distal recognition site for classical pathway convertase located in the C345C/netrin module of complement component C5", J Immunol, vol. 165, No. 2, pp. 1066-1073, (2000).

Schade, R, et al, "Egg yolk antibodies, State of the art and future prospects", Altex 13, supplement 96, pp. 5-9, (1996).

Schade, R, et al, "The production of avian (egg yolk) antibodies IgY. The report and recommendations of ECVAM workshop", Alternatives to laboratory animals (ATLA), vol. 24, pp. 925-934, (1996).

Schimmer, A.D, et al, "Receptor- and mitochondrial-mediated apoptosis in acute leukemia: a translational view", Blood, vol. 98, No. 13, pp. 3541-3553, (2001).

Schmidt-Acevedo, S, et al, "'LE cells' result from phagocytosis of apoptotic bodies induced by antinuclear antibodies", Journal of Autoimmunity, vol. 15, pp. 15-20, (2000).

Schmitt, C.A, et al, "Apoptosis is critical for drug response in vivo", Drug Resist Update, vol. 4, No. 2, pp. 132-134, (2001).

Sciavolino, P.J, et al, "Molecular biology of prostate development and prostate cancer", Ann Med, vol. 30, No. 4, pp. 357-368, (1998).

Scovassi, A.I, et al, "Poly(ADP-ribosylation) and apoptosis", Molecular and Cellular Biochemistry, vol. 199, pp. 125-137, (1999).

Semenkovich, C.F, et al, "A protein partially expressed on the surface of HepG2 cells that binds lipoproteins specifically is nucleolin", Biochemistry, vol. 29, No. 41, pp. 9708-9713, (1990).

Sen, D, et al, "Formation of parallel four-stranded complexes by guanine-rich motifs in DNA and its implications for meiosis", Nature, vol. 334, No. 6180, pp. 364-366, (1988).

Shall, S, et al, "Poly(ASP-ribose) polymerase-1: what have we learned from the deficient mouse model?", Mutat Research, vol. 460, No. 1, oo, 1-15, (2000).

(56) References Cited

OTHER PUBLICATIONS

Shall, S, "Poly (ADP-ribosylation)—a common control process?", Bioessays, vol. 24, No. 2, pp. 197-201, (2002).
Sharma, S, et al, "Development of inhalational agents for oncologic use", J Clin Oncol, vol. 19, No. 6, pp. 1839-1847, (2001).
Sharp, P.A, "RNA interference—2001" Genes Dev, vol. 15, No. 5, pp. 485-490, (2001).
Sharp, P.A, et al, "Molecular biology. RNA interference", Science, vol. 287, No. 5462, pp. 2431-2433, (2000).
Shaw, J.P, et al, "Modified deoxyoligonucleotides stable to exonuclease degradation in serum", Nucleic Acids Res, vol. 19, No. 4, pp. 747-750, (1991).
Sherwood, J.K. et al., "Controlled antibody delivery systems", Biotechnology, vol. 10, No. 11, pp. 1446-1449, (1992).
Shi, S.R, et al, "Antigen retrieval immunohistochemistry: past, present, and future", J Histochem Cytochem, vol. 45, pp. 327-343, (1997).
Shi, S.R, et al, "Antigen retrieval techniques: current perspectives", J Histochem Cytochem, vol. 49, pp. 931-937, (2001).
Shiokawa, D, et al, "Inhibitors of poly(ADP-ribose) polymerase suppress nuclear fragmentation and apoptotic-body formation during apoptosis in HL-60 cells", FEBS Letters, vol. 413, No. 1, pp. 99-103, (1997).
Simbulan-Rosenthal, C.M, et al, "Involvement of PARP and poly(ADP-ribosyl)ation in the early stages of apoptosis and DNA replication", Mol Cell Biochem, vol. 193, No. 1-2, pp. 137-148, (1999).
Sirri, V, et al, "Amount variability of total and individual Ag-NOR proteins in cells stimulated to proliferate", Histochem Cytochem, vol. 43, No. 9, pp. 887-893, (1995).
Skulstad, S, et al, "Labeling of surface proteins of herpes simplex virus type 1 using a modified biotin-streptavidin system", Virus Research, vol. 37, No. 3, pp. 253-270, (1995).
Smulson, M.E, et al, "Roles of poly(ADP-ribosyl)ation and PARP in apoptosis, DNA repair, genomic stability and functions of p53 and E2F-1", Adv Enzyme Regul, vol. 40, pp. 183-215, (2000).
Sohn, J.H, et al, "Caspase-3/CPP32 immunoreactivity and its correlation with frequency of apoptotic bodies in human prostatic carcinomas and benign nodular hyperplasias", Histopathology, vol. 37, No. 6, pp. 555-560, (2000).
Soldani, C. et al., "Poly(ADP-ribose) polymerase cleavage during apoptosis: when and where?", Exp Cell Research, vol. 269, No. 2, pp. 193-201, (2001).
Soldani, C. et al., "Two-color fluorescence detection of Poly (ADP-ribose) polymerase-1 (PARP-1) cleavage and DNA strand breaks in etoposide-induced apoptotic cells", Eur J Histochem, vol. 45, No. 4, pp. 389-392, (2001).
Sorokina, E.A, et al, "Cloning and preliminary characterization of a calcium-binding protein closely related to nucleolin on the apical surface of inner medullary collecting duct cells", J Biol Chem, vol. 274, No. 39, pp. 27491-27496, (1999).
Sperandio, S, et al, "An alternative, nonapoptotic form of programmed cell death", Proc Natl Acad Science USA, vol. 97, No. 26, pp. 14376-14381, (2000).
Srinivasan, S.K, et al, "Review of in vivo pharmacokinetics and toxicology of phosphorothioate oligonucleotides", J Clin Lab Anal, vol. 9, No. 2, pp. 129-137, (1995).
Srivastava, M, et al, "Molecular dissection of nucleolin's role in growth and cell proliferation: new insights", FASEB J, vol. 13, No. 14, pp. 1911-1922, (1999).
Stegh, A.H, et al, "DEDD, a novel death effector domain-containing protein, targeted to the nucleolus", EMBO J, vol. 17, No. 20, pp. 5974-5986, (1998).
Stein, C.A, "Is irrelevant cleavage the price of antisense efficacy?", Pharmacol Ther, vol. 85, No. 3, pp. 231-236, (2000).
Stein, C.A. "Keeping the biotechnology of antisense in context", Nat. Biotechnol, vol. 17, No. 3, pp. 209, (1999).
Stein, C.A, et al, "Phosphorothioate oligodeoxynucleotides-antisense inhibitors of gene expression?", Pharmacol Ther, vol. 52, No. 3, pp. 365-384, (1991).
Stone, K.R, et al, "Isolation of a human prostate carcinoma cell line (DU 145)", Int J Cancer, vol. 21, pp. 274-281, (1978).
Stroun, M, et al, "About the possible orgin and mechanism of circulating DNA apoptosis and active DNA release", Clin Chim Acta, vol. 313, No. 1-2, pp. 139-142, (2001).
Stryer, L, "Levels of structure in protein architecture", Biochemistry, Third Edition, chapter 2, pp. 31-33, W.H. Freeman Company, New York, (1988).
Summerton, J, et al, "Morpholino antisense oligomers: design, preparation, and properties", Antisense Nucleic Acid Drug Development, vol. 7, No. 3, pp. 187-195, (1997).
Sundquist, W.I, et al, "Telomeric DNA dimerizes by formation of guanine tetrads between hairpin loops", Nature, vol. 342, No. 6251, pp. 825-829, (1989).
Sundquist, W.I, et al, "Evidence for interstrand quadruplex formation in the dimerization of human immunodeficiency virus 1 genomic RNA", Proc Natl Acad Science USA, vol. 90, No. 8, pp. 3393-3397, (1993).
Sutton, V.R, et al, "Initiation of apoptosis by granzyme B requires direct cleavage of bid, but not direct granzyme B-mediated caspase activation", J Exp Med, vol. 192, No. 10, pp. 1403-1413, (2000).
Symons, R.H. "Small catalytic RNAs", Annual Review Biochem, vol. 61, pp. 641-671, (1992).
Takahashi, T, et al, "p53: a frequent target for genetic abnormalities in lung cancer", Science, vol. 246, pp. 491-494, (1989).
Tanaka, Y, et al, "Inhibition and down-regulation of poly(ADP-ribose) polymerase results in a marked resistance of HL-60 cells to various apoptosis-inducers", Cell Mol Biol, vol. 41, No. 6, pp. 771-781, (1995).
Templin, M.V, et al, "Pharmacokinetic and toxicity profile of a phosphorothioate oligonucleotide following inhalation delivery to lung in mice", Antisense Nucleic Acid Drug Dev, vol. 10, No. 5, pp. 359-368, (2000).
Tentori, L, et al, "Potential clinical applications of poly(ADP-ribose) polymerase (PARP) inhibitors", Pharmacol Res, vol. 45, No. 2, pp. 73-85, (2002).
Thornberry, N.A, et al, "Caspases: enemies within", Science, vol. 281, pp. 1312-1316, (1998).
Tockman, M.S, et al, "Prospective detection of preclinical lung cancer: results from two studies of heterogeneous nuclear ribonucleoprotein A2/B1 overexpression", Clin Cancer Research, vol. 3, No. 12, pt. 1, pp. 2237-2246, (1997).
Tockman, M.S, et al, "Sensitive and specific monoclonal antibody recognition of human lung cancer antigen on preserved sputum cells: a new approach to early lung cancer detection", J Clin Oncol, vol. 6, No. 11, pp. 1685-1693, (1988).
Tormanen, U, et al, "Enhanced apoptosis predicts shortened survival in non-small cell lung carcinoma", Cancer Research, vol. 55, No. 23, pp. 5595-5602, (1995).
Trere, D, "AgNOR staining and quantification", Micron, vol. 31, No. 2, pp. 127-131, (2000).
Tu G.C, et al, "Tetranucleotide GGGA motif in primary RNA transcripts. Novel target site for antisense design", J Biol Chem, vol. 273, No. 39, pp. 25125-25131, (1998).
Tuteja, N, et al, "Human DNA helicase IV is nucleolin, an RNA helicase modulated by phosphorylation", Gene, vol. 160, No. 2, pp. 143-148, (1995).
Tuteja, R, et al, "Nucleolin: a multifunctional major nucleolar phosphoprotein", Crit Rrev Biochem Mol Biol, vol. 33, pp. 407-436, (1998).
van de Loosdrecht, A.A, et al, "A tetrazolium-based colorimetric MTT assay to quantitate human monocyte mediated cytotoxicity against leukemic cells from cell lines and patients with acute myeloid leukemia", J Immunol Methods, vol. 174, pp. 311-320, (1994).
Waggoner, S, et al, "Viral ribonucleoprotein complex formation and nucleolar-cytoplasmic relocalization of nucleolin in poliovirus-infected cells", J Virol, vol. 72, No. 8, pp. 6699-6709, (1998).
Wang, W, et al, "A comparison of guanosine-quartet inhibitory effects versus cytidine homopolymer inhibitory effects on rat neointimal formation", Antisense Nucleic Acid Drug Development, vol. 8, No. 3, pp. 227-236, (1998).

(56) References Cited

OTHER PUBLICATIONS

Wang, Y, et al, "Regulation of dna replication after heat shock by replication protein a-nucleolin interactions", J Biol Chem, vol. 276, No. 23, pp. 20579-20588, (2001).

Wang, Y, et al, "Solution structure of the human telomeric repeat d[AG3(T2AG3)3] G-tetraplex", Structure, vol. 1, No. 4, pp. 263-282, (1993).

Wang, Z.Q, et al, "PARP is important for genomic stability but dispensable in apoptosis", Genes Dev, vol. 11, No. 18, pp. 2347-2358, (1997).

Weisenberger, D, et al, "A possible mechanism for the inhibition of ribosomal RNA gene transcription furing mitosis", J Cell Biology, vol. 129, No. 3, pp. 561-575, (1995).

White, J.R, et al, "Phosphorothioate-capped antisense oligonucleotides to Ras GAP injibit cell proliferation and trigger apoptosis but fail to downregulate GAP gene expression", Biochem Biophys Res Commun, vol. 227, No. 1, pp. 118-124, (1996).

Whittles, C.E, et al, "Apoptotic and proliferative activity in the neoplastic progression of Barrett's oesophagus: a comparative study", The Journal of Pathology, vol. 187, issue 5, pp. 535-540, (1999).

Williamson, J.R, et al, "Monovalent cation-induced structure of telomeric DNA: the G-quartet model", Cell, vol. 59, No. 5, pp. 871-880, (1989).

Winter, G, et al, "Making antibodies by phage display technology", Annu Rev Immunol, vol. 12, pp. 433-455, (1994).

Wolters, D.A, et al, "An automated multidimensional protein identification technology for shotfun proteomics", Anal Chem, vol. 73, No. 23, pp. 5683-5690, (2001).

Wurzer, G, et al, "Increased resistance to anticancer therapy of mouse cells lacking the poly(ADP-ribose) polymerase attributable to up-regulation of the multidrug resistance gene product P-glycoprotein", Cancer Research, vol. 60, No. 15, pp. 4238-4244, (2000).

Wyatt, J.R, et al, "Combinatorially selected guanosine-quartet structure is a potent inhibitor of human immunodeficiency virus envelope-mediated cell fusion", Proc Natl Acad Science USA, vol. 91, No. 4, pp. 1356-1360, (1994).

Wyllie, A.H, et al, "Cell death: the significance of apoptosis", International Review of Cytology, vol. 68, pp. 251-306, (1980).

Wysocki, L.J, et al, ""Panning" for lymphocytes: a method for cell selection", Proc Natl Acad Sci USA, vol. 75, No. 6, pp, 2844-2848, (1978).

Xu, X, et al "Inhibition of DNA replication and induction of S phase cell cycle arrest by G-rich oligonucleotides", The Journal of Biological Chemistry, vol. 276, No. 46, pp. 43221-43230, (2001).

Xue, Z, et al, "The amino terminus of mammalian nucleolin specifically recognizes SV40 T-antigen type nuclear localization sequences", Eur J Cell Biol, vol. 62, No. 1, pp. 13-21, (1993).

Yanagida, M, et al, "Isolation and proteomic characterization of the major proteins of the nucleolin-binding ribonucleoprotein complexes", Proteomics, vol. 1, No. 11, pp. 1390-1404, (2001).

Yao, G.Q, et al, "Identification of two oligodeoxyribonucleotide binding proteins on plasma membranes of human cell lines", Biochemical Pharmacology, vol. 51, pp. 431-436, (1996).

Xiao-Ming, Y., "Signal transduction mediated by Bid, a pro-death Bcl-2 family proteins, connects the death receptor and mitochondria apoptosis pathways", Cell Research, vol. 10, No. 3, pp. 161-167, (2000).

European Search Report dated Oct. 25, 2006 for European application No. 03762073.9.

Mi, Y., et al., "Apoptosis in Leukemia cells is accompanied by alterations in the levels and localization of Nucleolin", The Journal of Biological Chemistry, vol. 278, No. 10, pp. 8572-8579, (2003).

Rosen, A., et al., "Autoantigens as substrates for apoptotic proteases: implications for the pathogenesis of systemic autoimmune disease", Cell Death and Differentiation, vol. 6, No. 1, pp. 6-12, (1999).

Masters, J.R.W., "Human cancer cell lines: fact and fantasy", Nature Reviews Molecular Cell Biology, vol. 1, pp. 233-236, (2000).

Gougeon, M-L. et al., "Programmed cell death in peripheral lymphocytes from HIV-Infected persons", The Journal of Immunology, vol. 156, pp. 3509-3520, (1996).

Mi, Y. et al., "Regulation of Nucleolin in U937 Cells Treated with UV-Light and Cytotoxic Drugs", Blood, vol. 98, No. 11, Part 2 of 2, Abstract No. 4223, (2001).

Destouches, D. et al., "Suppression of tumor growth and angiogenesis by a specific antagonist of the cell-surface expressed nucleolin", Plos One, vol. 3, issue 6, e2518, pp. 1-12, (2008).

Fogal, V. et al., "Cell surface nucleolin antagonist causes endothelial cell apoptosis and normalization of tumor vasculature", Angiogenesis, vol. 12, No. 1, pp. 91-100, (2009).

Ugrinova I. et al., "Inactivation of nucleolin leads to nucleolar disruption, cell cycle arrest and defects in centrosome duplication", BMC Molecular Biology, pp. 1-16, (2007).

Cylene Pharmaceuticals, Quarfloxin Nucleolus Targeting Agent (CX-3543), Quarfloxin QPLX/Nucleolin Inhibitor (CX-3543), 1 page, printed on Jan. 21, 2010.

ImmuPharma, Treatment for Cancer (IPP-204106), pp. 1-3, found at http://immupharma.com/cancer.html, printed on Jan. 21, 2010.

Invitation to Pay Additional Fees and International Fees and Partial Search Report dated Jul. 14, 2009 for PCT/US2008/088491.

Grinstein, E. et al., "Cellular signaling in normal and cancerous stem cells", Cellular Signaling, 19, pp. 2428-2433, (2007).

Grinstein, E. et al., "Nucleolin Regulates Gene Expression in CD34-positive Hematopoietic Cells", The Journal of Biological Chemistry, vol. 282, No. 17, pp. 12439-12449, (2007).

Soltysova, A. et al., "Cancer Stem Cells", Neoplasma, 52, 6, pp. 435-440, (2005).

Huang, E.H. et al., "Cancer stem cells: A new paradigm for understanding tumor progression and therapeutic resistance", Surgery, vol. 141, pp. 415-419, (2007).

Girvan, A.C. et al., "AGRO100 inhibits activation of nuclear factor-κB (NF-κB) by forming a complex with NF-κB essential modulator (NEMO) and nucleolin", Molecular Cancer Therapeutics, vol. 5, No. 7, pp. 1790-1799, (2006).

Christian, S. et al., "Nucleolin expressed at the cell surface is a marker of endothelial cells in angiogenic blood vessels", The Journal of Cell Biology, vol. 163, No. 4, pp. 871-878, (2003).

Clarke, M.F. et al., "Stem Cells: The Real Culprits in Cancer?", Scientific American, 295, 1, pp. 52-59, (2006).

Shah, K. et al., "AS1411, a novel DNA aptamer as a potential treatment of acute myelogenous leukaemia (AML)", Meeting Poster, 48th Annual Meeting of the American Society of Hematology, Orlando, FL, USA. Dec. 9-12, 2006.

Guo, K-T. et al., "A new technique for the isolation and surface immobilization of mesenchymal stem cells from whole bone marrow using high-specific DNA aptamers", Stem Cells, vol. 24, pp. 2220-2231, (2006).

Rubanyi, G.M., "The future of human gene therapy", Molecular Aspects of Medicine, vol. 22, pp. 113-142, (2001).

Verma, I.M. et al., "Gene therapy—promises, problems and prospects", Nature, vol. 389, pp. 239-242, (1997).

Friedmann, T. "Overcoming the obstacles to gene therapy", Scientific American, pp. 96-101, (1997).

Orkin, S.H. et al., "Report and recommendations of the panel to assess the NIH investment in research on gene therapy", NIH ad hoc committee, pp. 1-39, found at http://oba.od.nih.gov/oba/rac/panelrep.pdf, (1995).

Gura, T. "Systems for identifying new drugs are often faulty", Science, vol. 278, pp. 1041-1042, (1997).

Beckman, R.A. et al., "Antibody constructs in cancer therapy", Cancer, vol. 109, No. 2, pp. 170-179, (2007).

Kito, S. et al., "Cleavage of nucleolin and AgNOR proteins during apoptosis induced by anticancer drugs in human salivary gland cells", Journal of Oral Pathology & Medicine, vol. 34, pp. 478-485, (2005).

National Cancer Institute, Fact Sheet, "Targeted Cancer Therapies", U.S. Department of Health and Human Services, pp. 1-8, May 9, 2012.

Zhang, Y. et al., "A surface-charge study on cellular-uptake behavior of F3-peptide-conjugated iron oxide nanoparticles", Small, vol. 5, No. 17, pp. 1990-1996, (2009).

(56) References Cited

OTHER PUBLICATIONS

Orringer, D.A. et al., "In vitro characterization of a targeted, dye-loaded nanodevice for intraoperative tumor delineation", Neurosurgery, vol. 64, No. 5, pp. 965-972, (2009).
Cao, Z. et al., "Reversible cell-specific drug delivery with aptamer-functionalized liposomes", Angewaudte Chemie International Edition, vol. 48, issue 35, pp. 6494-6498, (2009).
Shieh, Y-A. et al., "Aptamer-based tumor-targeted drug delivery for photodynamic therapy", ACS Nano, vol. 4, No. 3, pp. 1433-1442, (2010).
Guo, J. et al., "Aptamer-functionalized PEG-PLGA nanoparticles for enhanced anti-glioma drug delivery", Biomaterials, vol. 32, pp. 8010-8020, (2011).
Aravind, A. et al., "AS1411 aptamer tagged PLGA-lecithin-PEG nanoparticles for tumor cell targeting and drug delivery", Biotechnology and Bioengineering, vol. 109, No. 11, pp. 2920-2931, (2012).
Xie, L., et al., "Bovine serum albumin nanoparticles modified with multilayers and aptamers for pH-responsive and targeted anticancer drug delivery", Journal of Materials Chemistry, vol. 22, pp. 6053-6060, (2012).
Kang, W.J. et al., "Multiplex imaging of single tumor cells using quantum-dot-conjugated aptamers", Small, vol. 5, No. 22, pp. 2519-2522, (2009).
Ko, M.H. et al., "In vitro derby imaging of cancer biomarkers using quantum dots", Small, vol. 5, No. 10, pp. 1207-1212, (2009).
Choi, J.H. et al., "DNA aptamer-passivated nanocrystals synthesis: A facile approach for nanoparticles-based cancer cell growth inhibition", Small, vol. 5, No. 6, pp. 672-675, (2009).
Ai, J. et al., "DNA G-quadruplex-templated formation of the fluorescent silver nanocluster and its application to bioimaging", Talanta, vol. 88, pp. 450-455, (2012).
Kim, J.K. et al., "Molecular imaging of a cancer-targeting theragnostics probe using a nucleolin aptamer- and microRNA-221 molecular beacon-conjugated nanoparticle", Biomaterials, vol. 33, pp. 207-217, (2012).
Hwang, D.W. et al., "A nucleolin-targeted multimodal nanoparticle imaging probe for tracking cancer cells using an aptamer", Journal of Nuclear Medicine, vol. 51, No. 1, pp. 98-105, (2010).
Takafuji, Y. et al., "Simple PEG modification of DNA aptamer based on copper ion coordination for tumor targeting", Journal of Biomaterials Science, vol. 22, pp. 1179-1195, (2011).
Jain, K.K. "Advances in the field of nanooncology", BMC Medicine, vol. 8, No. 83, pp. 1-11, (2010).
Portney, N.G. et al., "Nano-oncology: drug delivery, imaging, and sensing", Analytical and Bioanalytical Chemistry, vol. 384, No. 3, pp. 620-630, (2006).
Bates, P.J. et al., "G-rich oligonucleotides for cancer treatment", Methods in Molecular Biology, vol. 542, pp. 379-392, (2009).
Bates, P.J. et al., "Discovery and development of the G-rich oligonucleotide AS1411 as a novel treatment for cancer", Experimental and molecular pathology, vol. 86, No. 3, pp. 151-164, (2009).
Soundararajan, S. et al., "The nucleolin targeting aptamer AS1411 destabilizes Bcl-2 messenger RNA in human breast cancer cells", Cancer Research, vol. 68, No. 7, pp. 2358-2365, (2008).
Javier, D.J. et al., "Aptamer-targeted gold nanoparticles as molecular-specific contrast agents for reflectance imaging", Bioconjugate Chemistry, vol. 19, No. 6, pp. 1309-1312, (2008).
Euhus, D.M. et al., "Tumor measurement in the nude mouse", Journal of Surgical Oncology, vol. 31, issue 4, pp. 229-234, (1986).
Tomayko, M.M. et al., "Determination of subcutaneous tumor size in athymic (nude) mice", Cancer Chemotherapy and Pharmacology, vol. 24, issue 3, pp. 148-154, (1989).
Mosmann, T. "Rapid colorimetric assay for cellular growth and survival: application to proliferation and cytotoxicity assays", Journal of Immunological Methods, vol. 65, issue 1-2, pp. 55-63, (1983).
Vermes, I. et al., "A novel assay for apoptosis. Flow cytometric detection of phosphatidylserine expression on early apoptotic cells using fluorescein labeled Annexin V", Journal of Immunological Methods, vol. 184, No. 1, pp. 39-51, (1995).
Reyes-Reyes, E.M. et al., "A new paradigm for aptamer therapeutic AS1411 action: uptake by macropinocytosis and its stimulation by a nucleolin-dependent mechanism", Cancer Research, vol. 70, No. 21, pp. 8617-8629, (2010).
Sprague, J.E. et al., "Noninvasive imaging of osteoclasts in parathyroid hormone-induced osteolysis using a 64Cu-labeled RGD peptide", Journal of Nuclear Medicine, Society of Nuclear Medicine, vol. 48, No. 2, pp. 311-318, (2007).
Thayer, A.M. "Fabulous fluorine", Chemical and Engineering News, vol. 84, No. 23, pp. 15-24, (2006).
Shoemaker, R.H. "The NCI60 human tumour cell line anticancer drug screen", Nature Reviews Cancer, vol. 6, No. 10, pp. 813-823, (2006).
Andrianasolo, E.H. et al., "DNA methyl transferase inhibiting halogenated monoterpenes from the Madagascar red marine alga Portieria hornemannii", Journal of Natural Products, vol. 69, No. 4, pp. 576-579, (2006).
Egorin, M.J. et al., "In vitro metabolism by mouse and human liver preparations of halomon, an antitumor halogenated monoterpene", Cancer Chemother Pharmacol, vol. 41, No. 1, pp. 9-14, (1997).
Egorin, M.J. et al., "Plasma pharmacokinetics, bioavailability, and tissue distribution in CD2F1 mice of halomon, an antitumor halogenated monoterpene isolated from the red algae Portieria hornemannii", Cancer Chemother Pharmacol, vol. 39, No. 1-2, pp. 51-60, (1996).
Fuller, R.W. et al., "Isolation and structure/activity features of halomon-related antitumor monoterpenes from the red alga Portieria hornemannii", Journal of Medicinal Chemistry, vol. 37, No. 25, pp. 4407-4411, (1994).
Fuller, R.W. et al., "A pentahalogenated monoterpene from the red alga Portieria hornemannii produces a novel cytotoxicity profile against a diverse panel of human tumor cell lines", Journal of Medicinal Chemistry, vol. 35, No. 16, pp. 3007-3011, (1992).
Thomsen, M.K. et al., "SOX9 elevation in the prostate promotes proliferation and cooperates with PTEN loss to drive tumor formation", Cancer Research, vol. 70, No. 3, pp. 979-987, (2010).
Wang, H. et al., "SOX9 is expressed in human fetal prostate epithelium and enhances prostate cancer invasion", Cancer Research, vol. 68, No. 6, pp. 1625-1630, (2008).
Thomsen, M.K. et al., "Sox9 is required for prostate development", Developmental Biology, vol. 316, No. 2, pp. 302-311, (2008).
Acevedo, V.D. et al., "Inducible FGFR-1 activation leads to irreversible prostate adenocarcinoma and an epithelial-to-mesenchymal transition", Cancer Cell, vol. 12, No. 6, pp. 559-571, (2007).
Wang, H. et al., "SOX9 is expressed in normal prostate basal cells and regulates androgen receptor expression in prostate cancer cells", Cancer Research, vol. 67, No. 2, pp. 528-536, (2007).
Baniwal, S.K. et al., "Runx2 transcriptome of prostate cancer cells: insights into invasiveness and bone metastasis", Molecular Cancer, vol. 9, pp. 1-18, (2010).
Qi, J. et al., "Siah2-dependent concerted activity of HIF and FoxA2 regulates formation of neuroendocrine phenotype and neuroendocrine prostate tumors", Cancer Cell, vol. 18, No. 1, pp. 23-38, (2010).
Schaeffer, E.M. et al., "Androgen-induced programs for prostate epithelial growth and invasion arise in embryogenesis and are reactivated in cancer", Oncogene, vol. 27, No. 57, pp. 7180-7191, (2008).
Dudley, A.C. et al., "Calcification of multi-potent, prostate tumor endothelium", Cancer Cell, vol. 14, No. 3, pp. 201-211, (2008).
Thomsen, M.K. et al., "The role of Sox9 in prostate development", Differentiation, vol. 76, pp. 728-735, (2008).
Walker, I. et al., "Do molecularly targeted agents in oncology have reduced attrition rates?", Nature Reviews, Drug Discovery, vol. 8, pp. 15-16, (2009).
Workman, P. et al., "Minimally invasive pharmacokinetic and pharmacodynamic technologies in hypothesis-testing clinical trials of innovative therapies", Journal of the National Cancer Institute, vol. 98, No. 9, pp. 580-598, (2006).

(56) References Cited

OTHER PUBLICATIONS

Khleif, S.N. et al., "AACR-FDA-NCI Cancer Biomarkers Collaborative consensus report: advancing the use of biomarkers in cancer drug development", Clinical Cancer Research, vol. 16, pp. 3299-3318, (2010).

Linardou, H. et al., "Assessment of somatic k-RAS mutations as a mechanism associated with resistance to EGFR-targeted agents: a systematic review and meta-analysis of studies in advanced non-small-cell lung cancer and metastatic colorectal cancer", Lancet Oncology, vol. 9, No. 10, pp. 962-972, (2008).

Annunziata, C.M. et al., "PARP inhibitors in BRCA1 /BRCA2 germline mutation carriers with ovarian and breast cancer", F1000 Biology Reports, vol. 2, No. 10, pp. 1-4, (2010).

American Cancer Society, "Cancer Facts and Figures 2010" found at www.cancer.org/research/cancerfactsfigures/cancerfactsfigures/cancer-facts-and-figures-2010, pp. 1-62, (2010).

Bonkhoff, H. et al., "From pathogenesis to prevention of castration resistant prostate cancer", The Prostate, vol. 70, No. 1, pp. 100-112, (2010).

Huch, M. et al., "Sox9 marks adult organ progenitors", Nature Genetics, vol. 43, No. 1, pp. 9-10, (2011).

Scott, C.E. et al., "SOX9 induces and maintains neural stem cells", Nature Neuroscience, vol. 13, No. 10, pp. 1181-1189, (2010).

Mori-Akiyama, Y. et al., "SOX9 is required for the differentiation of paneth cells in the intestinal epithelium", Gastroenterology, vol. 133, No. 2, pp. 539-546, (2007).

Malki, S. et al., "Expression and biological role of the prostaglandin D synthase/SOX9 pathway in human ovarian cancer cells", Cancer Letters, vol. 255, No. 2, pp. 182-193, (2007).

Jiang, S.S. et al., "Upregulation of SOX9 in Lung Adenocarcinoma and Its Involvement in the Regulation of Cell Growth and Tumorigenicity", Clinical Cancer Research, vol. 16, pp. 4363-4373, (2010).

Cajaiba, M.M. et al., "Sox9 expression is not limited to chondroid neoplasms: variable occurrence in other soft tissue and bone tumors with frequent expression by synovial sarcomas", International Journal of Surgical Pathology, vol. 18, No. 5, pp. 319-323, (2010).

Stange, D.E. et al., "Expression of an ASCL2 related stem cell signature and IGF2 in colorectal cancer liver metastases with 11p15.5 gain", Gut, vol. 59, pp. 1236-1244, (2010).

Muller, P. et al., "SOX9 mediates the retinoic acid-induced HES-1 gene expression in human breast cancer cells", Breast Cancer Research Treatment, vol. 120, No. 2, pp. 317-326, (2010).

Passeron, T. et al., "Upregulation of SOX9 inhibits the growth of human and mouse melanomas and restores their sensitivity to retinoic acid", The Journal of Clinical Investigation, vol. 119, No. 4, pp. 954-963, (2009).

Yasui, W. et al., "Transcriptome dissection of gastric cancer: Identification of novel diagnostic and therapeutic targets from pathology specimens", Pathology International, vol. 59, pp. 121-136, (2009).

Lu, B. et al., "Analysis of SOX9 expression in colorectal cancer", American Journal of Clinical Pathology, vol. 130, No. 6, pp. 897-904, (2008).

Endo, Y. et al., "Role of Sox-9, ER81 and VE-cadherin in retinoic acid-mediated trans-differentiation of breast cancer cells", PLoS One, vol. 3, issue 7, pp. 1-11, (2008).

de Bont, J.M. et al., "Differential expression and prognostic significance of SOX genes in pediatric medulloblastoma and ependymoma identified by microarray analysis", Neuro-Oncology, vol. 10, No. 5, pp. 648-660, (2008).

Vidal, V.P.I. et al., "SOX9 expression is a general marker of basal cell carcinoma and adnexal-related neoplasms", Journal of Cutaneous Pathology, vol. 35, pp. 373-379, (2008).

Passeron, T. et al., "SOX9 is a key player in ultraviolet B-induced melanocyte differentiation and pigmentation", Proceedings of the National Academy of Sciences, vol. 104, No. 35, pp. 13984-13989, (2007).

Duhagon, M.A. et al., "Genomic profiling of tumor initiating prostatospheres", BMC Genomics, vol. 11, No. 324, pp. 1-16, (2010).

Yilmaz, O.H. et al., "Pten dependence distinguishes haematopoietic stem cells from leukaemia-initiating cells", Nature, vol. 441, pp. 475-482, (2006).

Yoo, C.B. et al., "Epigenetic therapy of cancer: past, present and future", Nature Reviews Drug Discovery, vol. 5, No. 1, pp. 37-50, (2006).

McCabe, M.T. et al., "Cancer DNA methylation: molecular mechanisms and clinical implications", Clinical Cancer Research, vol. 15, No. 12, pp. 3927-3937, (2009).

Piekarz, R.L. et al., "Epigenetic modifiers: basic understanding and clinical development", Clinical Cancer Research, vol. 15, No. 12, pp. 3918-3926, (2009).

Issa, J-P.J. et al., "Targeting DNA methylation", Clinical Cancer Research, vol. 15, No. 12, pp. 3938-3946, (2009).

Xu, B. et al., "An efficient synthesis of difluoropropargyl bromides", Synthesis, vol. 5, pp. 803-806, (2006).

Sigalotti, L. et al., "Epigenetic modulation of solid tumors as a novel approach for cancer immunotherapy", Seminars in Oncology, vol. 32, No. 5, pp. 473-478, (2005).

Budman, D.R. et al., "Identification of potentially useful combinations of epidermal growth factor receptor tyrosine kinase antagonists with conventional cytotoxic agents using median effect analysis", Anti-cancer Drugs, vol. 17, No. 8, pp. 921-928, (2006).

Yang, X. et al., "Near-infrared light-triggered, targeted drug delivery to cancer cells by aptamer gated nanovehicles", Advanced Materials, vol. 24, pp. 2890-2895, (2012).

International Search Report dated Sep. 19, 2012 for PCT application No. PCT/US2012/040577.

Akerman, M.E. et al., "Nanocrystal targeting in vivo", Proceedings of the National Academy of Sciences, vol. 99, No. 20, pp. 12617-12621, (2002).

Winer, I. et al., "F3-targeted cisplatin-hydrogel nanoparticles as an effective therapeutic that targets both murine and human ovarian tumor endothelial cells in vivo", Cancer Research, vol. 70, No. 21, pp. 8674-8683, (2010).

Dam, D.H.M. et al., "Direct observation of nanoparticle-cancer cell nucleus interactions", ACS Nano, vol. 6, No. 4, pp. 3318-3326, (2012).

Bruckner, R.C. et al., "The histone-like H protein of *Escherichia coli* is ribosomal protein S3", Nucleic Acids Research, vol. 17, No. 8, pp. 3145-3161, (1989).

"Nucleolin Antibody—Antibody product information from all suppliers", Labome the World of Laboratories, pp. 1-4, found at www.labome.com/gene/human/nucleolin-antibody.html, printed on Jun. 1, 2012.

Malik, M.T. et al., "Multifunctional gold nanoparticles linked with aptamers and fluorophores for breast cancer imaging and therapy", American Association of Cancer Research Annual Meeting, Mar. 31-Apr. 4, 2012, Chicago, IL Abstract #5688.

Subramanian, D. et al., "Induction of macropinocytosis and cell death in neuroblastoma cells treated with AS1411", Research Louisville 2011, University of Louisville, Louisville, Kentucky, Abstract #GRD-72.

Malik, M.T. et al., "Aptamers conjugated to gold nanoparticles and their potential for breast cancer imaging and therapy", Congressionally Directed Medical Research Programs, Era of Hope 2011, Orlando Florida, Aug. 2-5, 2011, Poster #P43-16.

Srivastava, M. et al., "Genomic organization and chromosomal localization of the human necleolin gene", The Journal of Biological Chemistry, vol. 265, No. 25, pp. 14922-14931, (1995).

Gattoni-Celli, S. et al., "Overexpression of nucleolin in engrafted acute myelogenous leukemia cells", American Journal of Hematology, vol. 84, issue 8, pp. 535-538, (2009).

Green, C. et al., "Anti-tumor efficacy and pharmacokinetics of the novel aptamer AS1411 in a continuous infusion nude rat xenograft model", Proceedings of the 101$^{st}$ Annual Meeting of the American Association for Cancer Research, Abstract No. 2614, Apr. 17-21, 2010.

Fernandes, D.J. et al., "Human anti-nucleolin antibodies with broad spectrum anticancer activity", Proceeding of the 103$^{rd}$ Annual Meeting of the American Association for Cancer Research, Abstract No. 4623, Mar. 31-Apr. 4, 2012.

(56) References Cited

OTHER PUBLICATIONS

Laber, D.A. et al., "Extended phase I study of AS1411 in renal and non-small cell lung cancers", Journal of Clinical Oncology, ASCO Annual Meeting Proceedings, vol. 24, No. 18S, Abstract No. 13098, (2006).

Chames, P. et al., "Therapeutic antibodies: successes, limitations and hopes for the future", British Journal of Pharmacology, vol. 157, pp. 220-233, (2009).

Huang, Y. et al., "The angiogenic function of nucleolin is mediated by vascular endothelial growth factor and nonmuscle myosin", Blood, vol. 107, No. 9, pp. 3564-3571, (2006).

Bates, P.J. "DNA Aptamers: Potential application in nanotechnology, drug delivery, therapy, & imaging", Mini-Symposium on Nanobiomotors, University of Kentucky, Abstract, 1 page, Mar. 26, 2012.

European Search Report for Application No. 15182208.7 dated Mar. 2, 2016.

6 Pages, Mar. 29, 2016, U.S. Appl. No. 14/059,211.

Hengge, U.R. et al., "Long-term chemotherapy of HIV-associated Kaposi's sarcoma with liposomal doxorubicin", European Journal of Cancer, vol. 37, pp. 878-883, (2001).

Orlikowsky, T.W. et al., "Dexamethasone inhibits CD4 T cell deletion mediated by macrophages from human immunodeficiency virus-infected persons", Journal of Infectious Diseases, vol. 184, No. 10, pp. 1328-1330, (2001).

17 Pages, Dec. 8, 2015, U.S. Appl. No. 14/059,211.

Jul. 19, 2016, U.S. Appl. No. 14/059,211.

Jul. 21, 2016, PCT/US2016/030985.

International Search Report dated Jul. 21, 2016 for PCT application No. PCT/US2016/030985.

Hua, X. et al., "Selective collection and detection of MCF-7 breast cancer cells using aptamer-functionalized magnetic beads and quantum dots based nano-bio-probes", Analytica Chimica Acta, vol. 788, pp. 135-140, (2013).

* cited by examiner

2HR POST INJECTION

6HR POST INJECTION

NON-TREATED

GOLD NANOPARTICLES

GNP-CRO (200nM)

GNP-AS1411 (200nM)

CRO-Cy5 (10uM)

AS1411-Cy5 (10uM)

GNP-Cy5-CRO (200nM)

GNP-Cy5-AS1411 (200nM)

US 9,452,219 B2

ANTI-NUCLEOLIN AGENT-CONJUGATED NANOPARTICLES

FEDERALLY SPONSORED RESEARCH OR DEVELOPMENT

This invention was made with Government support under of grant No. W81XWH-10-1-0053 awarded by the Department of Defense, U.S. Army Medical Research. The Government has certain rights in the invention.

BACKGROUND

Nucleolin [8] is an abundant, non-ribosomal protein of the nucleolus, the site of ribosomal gene transcription and packaging of pre-ribosomal RNA. This 710 amino acid phosphoprotein has a multi-domain structure consisting of a histone-like N-terminus, a central domain containing four RNA recognition motifs and a glycine/arginine-rich C-terminus, and has an apparent molecular weight of 110 kD. While nucleolin is found in every nucleated cell, the expression of nucleolin on the cell surface has been correlated with the presence and aggressiveness of neoplastic cells [3].

The correlation of the presence of cell surface nucleolin with neoplastic cells has been used for methods of determining the neoplastic state of cells by detecting the presence of nucleolin on the plasma membranes [3]. This observation has also provided new cancer treatment strategies based on administering compounds that specifically targets nucleolin [4].

Nucleic acid aptamers are short synthetic oligonucleotides that fold into unique three-dimensional structures that can be recognized by specific target proteins. Thus, their targeting mechanism is similar to monoclonal antibodies, but they may have substantial advantages over these, including more rapid clearance in vivo, better tumor penetration, non-immunogenicity, and easier synthesis and storage.

Guanosine-rich oligonucleotides (GROs) designed for triple helix formation are known for binding to nucleolin [5]. This ability to bind nucleolin has been suggested to cause their unexpected ability to effect antiproliferation of cultured prostate carcinoma cells [6]. The antiproliferative effects are not consistent with a triplex-mediated or an antisense mechanism, and it is apparent that GROs inhibit proliferation by an alternative mode of action. It has been surmised that GROs, which display the propensity to form higher order structures containing G-quartets, work by an aptamer mechanism that entails binding to nucleolin due to a shape-specific recognition of the GRO structure; the binding to cell surface nucleolin then induces apoptosis. The antiproliferative effects of GROs have been demonstrated in cell lines derived from prostate (DU145), breast (MDA-MB-231, MCF-7), or cervical (HeLa) carcinomas and correlates with the ability of GROs to bind cell surface nucleolin [6].

AS1411, a GRO nucleolin-binding DNA aptamer that has antiproliferative activity against cancer cells with little effect on non-malignant cells, was previously developed. AS1411 uptake appears to occur by macropinocytosis in cancer cells, but by a nonmacropinocytic pathway in nonmalignant cells, resulting in the selective killing of cancer cells, without affecting the viability of nonmalignant cells [9]. AS1411 was the first anticancer aptamer tested in humans and results from clinical trials of AS1411 (including Phase II studies in patients with renal cell carcinoma or acute myeloid leukemia) indicate promising clinical activity with no evidence of serious side effects. Despite the promising clinical results from Phase II studies, AS1411 did not perform as expected in Phase IIB studies, possibly due to the low potency of AS1411.

SUMMARY

In a first aspect, the present invention is a composition, comprising an anti-nucleolin agent conjugated to nanoparticles. The nanoparticles are non-magnetic.

In a second aspect, the present invention is a pharmaceutical composition for treating cancer, comprising a composition, comprising an anti-nucleolin agent conjugated to nanoparticles, and a pharmaceutically acceptable carrier.

In a third aspect, the present invention is a method of treating cancer, comprising administering an effective amount of the pharmaceutical composition of any of the preceding claims, to a patient in need thereof.

In a fourth aspect, the present invention is an agent for imaging, comprising the composition of any of the preceding claims, and a pharmaceutically acceptable carrier.

In a fifth aspect, the present invention is a method of imaging cancer in vivo, comprising administering the imaging agent of any of the preceding claims, to a subject and forming an image of the imaging agent present in the subject.

DEFINITIONS

The term "conjugated" means "chemically bonded to".

The term "anti-nucleolin oligonucleotides" refers to an oligonucleotide that binds to nucleolin.

The term "GI50" refers to the concentrations required to achieve 50% of cell growth inhibition. GI50 values may be determined by a cell proliferation/cytotoxicity assay (MTT) assay, described by Morgan [23], Girvan et al. [19] and Mosmann [20].

The term "equivalent aptamer concentration" refers to the concentration of anti-nucleolin oligonucleotide present in the conjugate.

Tumors and cancers include solid, dysproliferative tissue changes and diffuse tumors. Examples of tumors and cancers include melanoma, lymphoma, plasmocytoma, sarcoma, glioma, thymoma, leukemia, breast cancer, prostate cancer, colon cancer, liver cancer, esophageal cancer, brain cancer, lung cancer, ovary cancer, endometrial cancer, bladder cancer, kidney cancer, cervical cancer, hepatoma, and other neoplasms. For more examples of tumors and cancers, see, for example Stedman [1].

"Treating a tumor" or "treating a cancer" means to significantly inhibit growth and/or metastasis of the tumor or cancer. Growth inhibition can be indicated by reduced tumor volume or reduced occurrences of metastasis. Tumor growth can be determined, for example, by examining the tumor volume via routine procedures (such as obtaining two-dimensional measurements with a dial caliper). Metastasis can be determined by inspecting for tumor cells in secondary sites or examining the metastatic potential of biopsied tumor cells in vitro.

A "chemotherapeutic agent" is a chemical compound that can be used effectively to treat cancer in humans.

A "pharmaceutically acceptable carrier" includes any and all solvents, dispersion media, coatings, antibacterial and antifungal agents, isotonic and absorption delaying agents which are compatible with pharmaceutical administration. Preferred examples of such carriers or diluents include water, saline, Ringer's solutions and dextrose solution. Supplementary active compounds can also be incorporated into the compositions.

"Medicament," "therapeutic composition" and "pharmaceutical composition" are used interchangeably to indicate a compound, matter, mixture or preparation that exerts a therapeutic effect in a subject.

"Antibody" is used in the broadest sense and refers to monoclonal antibodies, polyclonal antibodies, multispecific antibodies, antibody fragments and chemically modified antibodies, where the chemical modification does not substantially interfere with the selectivity and specificity of the antibody or antibody fragment.

An "anti-nucleolin agent" includes any molecule or compound that interacts with nucleolin. Such agents include for example anti-nucleolin antibodies, aptamers such GROs and nucleolin targeting proteins.

BRIEF DESCRIPTION OF THE DRAWINGS

FIG. 1A is a graph of tumor volume of in vivo xenograft tumors in nude mice treated with various agents, while

DETAILED DESCRIPTION

Figure 1A:
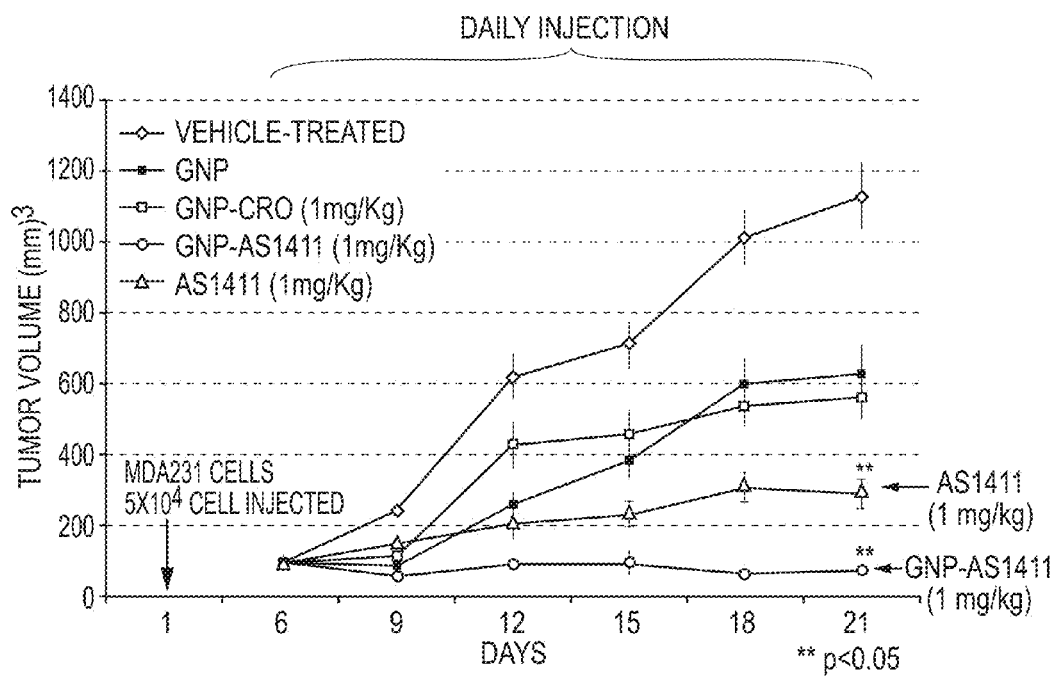

The present invention makes use of the discovery that anti-nucleolin agents, conjugated to particles, such as aptamer conjugated to gold nanoparticles, have an antiproliferative effect on cancer and tumors. Furthermore, aptamer conjugated gold nanoparticels in particular have a similar or greater antiproliferative effect than the aptamer (anti-nucleolin oligonucleotide) alone, demonstrating similar effects at only 1/10 to 1/100 the dosage. Furthermore, these same agents, preferably having a fluorescent dye conjugated to the particle or attached to the anti-nucleolin agent, may also be used as imaging agents, both in vivo and ex vivo.

Anti-nucleolin agents include (i) aptamers, such as GROs; (ii) anti-nucleolin antibodies; and (iii) nucleolin targeting proteins. Examples of aptamers include guanosine-rich oligonucleotides (GROs). Examples of suitable oligonucleotides and assays are also given in Miller et al. [7]. Characteristics of GROs include:

(1) having at least 1 GGT motif,
(2) preferably having 4-100 nucleotides, although GROs having many more nucleotides are possible,
(3) optionally having chemical modifications to improve stability.

Especially useful GROs form G-quartet structures, as indicated by a reversible thermal denaturation/renaturation profile at 295 nm [6]. Preferred GROs also compete with a telomere oligonucleotide for binding to a target cellular protein in an electrophoretic mobility shift assay [6]. In some cases, incorporating the GRO nucleotides into larger nucleic acid sequences may be advantageous; for example, to facilitate binding of a GRO nucleic acid to a substrate without denaturing the nucleolin-binding site. Examples of oligonucleotides are shown in Table 1; preferred oligonucleotides include SEQ IDs NOs: 1-7; 9-16; 19-30 and 31 from Table 1.

TABLE 1

Non-antisense GROs that bind nucleolin and non-binding controls[1,2,3].

| GRO | Sequence | SEQ ID NO: |
|---|---|---|
| GRO29A[1] | tttggtggtg gtggttgtgg tggtggtgg | 1 |
| GRO29-2 | tttggtggtg gtggttttgg tggtggtgg | 2 |
| GRO29-3 | tttggtggtg gtggtggtgg tggtggtgg | 3 |
| GRO29-5 | tttggtggtg gtggtttggg tggtggtgg | 4 |
| GRO29-13 | tggtggtggt ggt | 5 |
| GRO14C | ggtggttgtg gtgg | 6 |
| GRO15A | gttgtttggg gtggt | 7 |
| GRO15B[2] | ttgggggggg tgggt | 8 |
| GRO25A | ggttggggtg ggtggggtgg gtggg | 9 |
| GRO26B[1] | ggtggtggtg gttgtggtgg tggtgg | 10 |
| GRO28A | tttggtggtg gtggttgtgg tggtggtg | 11 |
| GRO28B | tttggtggtg gtggtgtggt ggtggtgg | 12 |
| GRO29-6 | ggtggtggtg gttgtggtgg tggtggttt | 13 |
| GRO32A | ggtggttgtg gtggttgtgg tggttgtggt gg | 14 |
| GRO32B | tttggtggtg gtggttgtgg tggtggtggt tt | 15 |
| GRO56A | ggtggtggtg gttgtggtgg tggtggttgt ggtggtggtg gttgtggtgg tggtgg | 16 |
| CRO | tttcctcctc ctccttctcc tcctcctcc | 18 |
| GRO A | ttagggttag ggttagggtt aggg | 19 |
| GRO B | ggtggtggtg g | 20 |
| GRO C | ggtggttgtg gtgg | 21 |
| GRO D | ggttggtgtg gttgg | 22 |
| GRO E | gggttttggg | 23 |
| GRO F | ggttttggtt ttggttttgg | 24 |
| GRO G[1] | ggttggtgtg gttgg | 25 |
| GRO H[1] | ggggttttgg gg | 26 |
| GRO I[1] | gggttttggg | 27 |
| GRO J[1] | ggggttttgg ggttttgggg ttttgggg | 28 |
| GRO K[1] | ttggggttgg ggttggggtt gggg | 29 |
| GRO L[1] | gggtgggtgg gtgggt | 30 |
| GRO M[1] | ggttttggtt ttggttttgg ttttgg | 31 |
| GRO N[2] | tttcctcctc ctccttctcc tcctcctcc | 32 |
| GRO O[2] | cctcctcctc cttctcctcc tcctcc | 33 |
| GRO P[2] | tggggt | 34 |
| GRO Q[2] | gcatgct | 35 |
| GRO R[2] | gcggtttgcg g | 36 |
| GRO S[2] | tagg | 37 |
| GRO T[2] | ggggttgggg tgtggggttg ggg | 38 |

[1] Indicates a good plasma membrane nucleolin-binding GRO.
[2] Indicates a nucleolin control (non-plasma membrane nucleolin binding).
[3] GRO sequence without 1 or 2 designations have some anti-proliferative activity.

Any antibody that binds nucleolin may also be used. In certain instances, monoclonal antibodies are preferred as they bind single, specific and defined epitopes. In other instances, however, polyclonal antibodies capable of interacting with more than one epitope on nucleolin may be used. Many anti-nucleolin antibodies are commercially available, and are otherwise easily made. Table 2 list a few commercially available anti-nucleolin antibodies.

TABLE 2 commercially available anti-nucleolin antibodies

| Antibody | Source | Antigen source |
|---|---|---|
| p7-1A4 Mouse monoclonal antibody (mAb) | Developmental Studies Hybridoma Bank | Xenopus laevis oocytes |
| Sc-8031 mouse mAb | Santa Cruz Biotech | human |
| Sc-9893 goat polyclonal Ab (pAb) | Santa Cruz Biotech | human |
| Sc-9892 goat pAb | Santa Cruz Biotech | human |
| Clone 4E2 mouse mAb | MBL International | human |
| Clone 3G4B2 mouse mAb | Upstate Biotechnology | dog (MDCK cells) |
| Nucleolin, Human (mouse mAb) | MyBioSource | human |
| Purified anti-Nucleolin-Phospho, Thr76/Thr84 (mouse mAb) | BioLegend | human |
| Rabbit Polyclonal Nucleolin Antibody | Novus Biologicals | human |
| Nucleolin (NCL, C23, FLJ45706, FLJ59041, Protein C23) Mab Mo xHu | US Biological | human |
| Nucleolin (NCL, Nucl, C23, FLJ45706, Protein C23) Pab Rb xHu | US Biological | human |
| Mouse Anti-Human Nucleolin Phospho-Thr76/Thr84 Clone 10C7 mAb | Cell Sciences | human |

TABLE 2-continued commercially available anti-nucleolin antibodies

| Antibody | Source | Antigen source |
|---|---|---|
| Anti-NCL/Nucleolin (pAb) | LifeSpan Biosciences | human |
| NCL purified MaxPab mouse polyclonal antibody (B02P) | Abnova | human |
| NCL purified MaxPab rabbit polyclonal antibody (D01P) | Abnova | human |
| NCL monoclonal antibody, clone 10C7 (mouse mAb) | Abnova | human |
| Nucleolin Monoclonal Antibody (4E2) (mouse mAb) | Enzo Life Sciences | human |
| Nucleolin, Mouse Monoclonal Antibody | Life Technologies Corporation | human |
| NCL Antibody (Center E443) (rabbit pAb) | Abgent | human |
| Anti-Nucleolin, clone 3G4B2 (mouse mAb) | EMD Millipore | human |
| NCL (rabbit pAb) | Proteintech Group | human |
| Mouse Anti-Nucleolin Monoclonal Antibody, Unconjugated, Clone 3G4B20 | Active Motif | human |
| Nsr1p - mouse monoclonal | EnCor Biotechnology | human |
| Nucleolin (mouse mAb) | Thermo Scientific Pierce Products | human |
| Nucleolin [4E2] antibody (mouse mAb) | GeneTex | human |

Nucleolin targeting proteins are proteins, other than antibodies, that specifically and selectively bind nucleolin. Examples include ribosomal protein S3, tumor-homing F3 peptides [26, 27] and myosin H9 (a non-muscle myosin that binds cell surface nucleolin of endothelial cells in angiogenic vessels during tumorigenesis).

Anti-nucleolin agents may be conjugated to particles made of a variety of materials solid materials, including (1) metals and elements; (2) oxides; (3) semiconductors; and (4) polymers. Metals and elements, preferbly non-magnetic metals and elements, include gold, silver, palladium, iridium, platinum and alloys thereof; elements include silicon, boron and carbon (such as diamond, graphene and carbon nanotubes), and solid compounds thereof. Oxides include titanium dioxide, silicon dioxide, zinc oxide, iron oxide, zirconium oxide, magnesium oxide, aluminum oxide and complex oxides thereof, such as barium titanate. Semiconductors include quantum dots, zinc sulfide, silicon/germanium alloys, boron nitride, aluminum nitride, and solid solutions thereof. Polymers include polyethylenes, polystyrenes, polyacrylamide, polyacrylates and polymethacrylates, and polysiloxanes. Preferably, the particles are non-toxic. The particles are preferably nanoparticles having an average particle diameter of 1-100 nm, more preferably 1-50 nm, including 5, 10, 15, 20, 25, 30, 35, 40, 45, 50, 55, 60, 65, 70, 75, 80, 85, 90 and 95 nm.

Oligonucleotides and proteins have been attached to solid materials, such metals and elements, oxides, semiconductors and polymers, by a variety of techniques. These same techniques may be used to attached anti-nucleolin agents to particles. Further attachment of dyes to the anti-nucleolin agent conjugated nanoparticles (conjugates), such as cyanine dyes, allows the conjugates to be used as imaging agents, both in vivo and ex vivo.

Anti-nucleolin agent conjugated nanoparticles may be used to formulate a pharmaceutical composition for treating cancer and tumors, and targeting cancer cells expressing cell surface nucleolin, by forming mixtures off the anti-nucleolin agent conjugated nanoparticles and a pharmaceutically acceptable carrier, such as a pharmaceutical composition. Methods of treating cancer in a subject include administering a therapeutically effective amount of an anti-nucleolin agent conjugated nanoparticles.

Particularly preferred compositions are aptamers conjugated to gold nanoparticles. Gold nanoparticles (GNPs) exhibit low toxicity, versatile surface chemistry, light absorbing/scattering properties, and tunable size. Aptamers effectively cap gold particles and prevent aggregation, are safe, stable, easy to synthesize, and non-immunogenic. Aptamer conjugated GNPs offer many advantages over alternative approaches, such as enhanced antiproliferative activity in cancer cells over AS1411 alone and improved efficacy in vivo, causing durable regression of established breast cancer xenograft in mice, without evidence of side effects. Aptamer conjugated GNP are highly selective for cancer cells over normal cells, and when attached to cyanine dyes are excellent imaging agents, for example Cy2, Cy3, Cy5, Cy®5.5, Cy7, Alexa Fluor® 680, Alexa Fluor 750, IRDye® 680, and IRDye® 800CW (LI-COR Biosciences, Lincoln, Nebr.). Aptamer conjugated GNP may be used as an imaging agent, and may be administered as compositions which further contain a pharmaceutically acceptable carrier. The imaging agent may be administered to a subject in a method of imaging cancer in vivo, to form an image of the imaging agent present in the subject.

The amounts and ratios of compositions described herein are all by weight, unless otherwise stated. Accordingly, the number of anti-nucleolin agents per nanoparticle may vary when the weight of the nanoparitcle varies, even when the equivalent anti-nucleolin agent concentration (or equivalent aptamer concentration) is otherwise the same. For example, the number of anti-nucleolin agent molecules per nanoparticle may vary from 2 to 10,000, or 10 to 1000, including 20, 30, 40, 50, 60, 70, 80, 90, 100, 200, 300, 400, 500, 600, 700, 800 and 900.

A pharmaceutical composition is formulated to be compatible with its intended route of administration, including intravenous, intradermal, subcutaneous, oral, inhalation, transdermal, transmucosal, and rectal administration. Solutions and suspensions used for parenteral, intradermal or subcutaneous application can include a sterile diluent, such as water for injection, saline solution, polyethylene glycols, glycerine, propylene glycol or other synthetic solvents; antibacterial agents such as benzyl alcohol or methyl parabens; antioxidants such as ascorbic acid or sodium bisulfite; buffers such as acetates, citrates or phosphates, and agents for the adjustment of tonicity such as sodium chloride or dextrose. The pH can be adjusted with acids or bases, such as hydrochloric acid or sodium hydroxide.

Pharmaceutical compositions suitable for injection include sterile aqueous solutions or dispersions for the extemporaneous preparation of sterile injectable solutions or dispersion. For intravenous administration, suitable carriers include physiological saline, bacteriostatic water, CREMOPHOR EL® (BASF; Parsippany, N.J.) or phosphate buffered saline (PBS). In all cases, the composition must be sterile and should be fluid so as to be administered using a syringe. Such compositions should be stable during manufacture and storage and are preferably preserved against contamination from microorganisms such as bacteria and fungi. The carrier can be a dispersion medium containing, for example, water, polyol (such as glycerol, propylene glycol, and liquid polyethylene glycol), and other compatible, suitable mixtures. Various antibacterial and anti-fungal agents, for example, parabens, chlorobutanol, phenol, ascorbic acid, and thimerosal, can contain microorganism contamination. Isotonic agents such as sugars, polyalcohols, such as mannitol, sorbitol, and sodium chloride can be included in the composition. Compositions that can delay absorption include agents such as aluminum monostearate and gelatin.

Sterile injectable solutions can be prepared by incorporating the active agents, and other therapeutic components, in the required amount in an appropriate solvent with one or a combination of ingredients as required, followed by sterilization. Methods of preparation of sterile solids for the preparation of sterile injectable solutions include vacuum drying and freeze-drying to yield a solid.

The pharmaceutical composition described herein may further comprise other therapeutically active compounds, and/or may be used in conjuction with physical techniques as noted herein which are suitable for the treatment of cancers and tumors. Examples of commonly used therapeutically active compounds include vinorelbine (Navelbine®), mytomycin, camptothecin, cyclyphosphamide (Cytoxin®), methotrexate, tamoxifen citrate, 5-fluorouracil, irinotecan, doxorubicin, flutamide, paclitaxel (Taxol®), docetaxel, vinblastine, imatinib mesylate (Gleevec®), anthracycline, letrozole, arsenic trioxide (Trisenox®), anastrozole, triptorelin pamoate, ozogamicin, irinotecan hydrochloride (Camptosar®), BCG, live (Pacis®), leuprolide acetate implant (Viadur), bexarotene (Targretin®), exemestane (Aromasin®), topotecan hydrochloride (Hycamtin®), gemcitabine HCL (Gemzar®), daunorubicin hydrochloride (Daunorubicin HCL®), gemcitabine HCL (Gemzar®), toremifene citrate (Fareston), carboplatin (Paraplatin®), cisplatin (Platinol® and Platinol-AQ®) oxaliplatin and any other platinum-containing oncology drug, trastuzumab (Herceptin®), lapatinib (Tykerb®), gefitinb (Iressa®), cetuximab (Erbitux®), panitumumab (Vectibix®), temsirolimus (Torisel®), everolimus (Afinitor®), vandetanib (Zactima™), vemurafenib (Zelboraf™), crizotinib (Xalkori®), vorinostat (Zolinza®), bevacizumab (Avastin®), radiation therapy, hyperthermia, gene therapy and photodynamic therapy.

In the treatment of cancer, an appropriate dosage level of the therapeutic agent will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. The compounds may be administered on a regimen of 1 to 4 times per day, preferably once or twice per day. Administration by continuous infusion is also preferable. All amounts and concentrations of anti-nucleolin oligonucleotide conjugated gold nanoparticles are based on the amount or concentration of anti-nucleolin oligonucleotide only.

Pharmaceutical preparation may be pre-packaged in ready-to-administer form, in amounts that correspond with a single dosage, appropriate for a single administration referred to as unit dosage form. Unit dosage forms can be enclosed in ampoules, disposable syringes or vials made of glass or plastic.

However, the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the patient undergoing therapy.

Examples

AS1411-linked gold nanoparticles for treating cancer and for cancer imaging we synthasized. Studies to assess the anticancer activity of AS1411 linked to 5 nm gold nanoparticles indicate that the conjugates have greatly enhanced antiproliferative effects on breast cancer cells compared to AS1411 (SEQ ID NO. 10) alone. Microscopic examination revealed increased uptake in breast cancer cells for GNP-AS1411 compared to GNP alone or GNP conjugated to a control oligonucleotide. In addition, GNP-AS1411 induced breast cancer cell vacuolization and death, similar to that seen at higher concentrations of AS1411. The GI50 values for AS1411 conjugated GNP against breast cancer cells are in the 50-250 nM range, compared to 1-10 uM range for unconjugated AS1411 (equivalent aptamer concentration). Studies indicate that these AS1411-GNPs have selective uptake in tumor tissue following systemic administration in mice. Moreover, AS1411-GNPs retained the cancer-selectivity of AS1411 and had no effect on non-malignant cells.

Pilot in vivo studies in mice with MDA-MB-231 (MDA231) xenografts have shown that intravenous administration of AS1411-GNPs at 1 mg/kg/day for 14 days could almost completely inhibit tumor growth. These activities were aptamer-related because GNPs conjugated to control DNA had little or no activity, in terms of internalization in breast cancer cells, uptake in xenografts, and inhibitory effects on breast cancer cells growing in culture or in vivo.

Preparation of Aptamer Conjugated Gold Nanoparticles (GNP)

The aptamers AS1411 and CRO (the control oligonucleotide) with 5' prime thiol modification and or 3' fluorophore Cy5 were purchased from Integrated DNA Technologies (IDT).

```
AS1411 with thiol link at 5':
5'-/5ThioMC6-D/TTT TTT GGT GGT GGT GGT

TGT GGT GGT GGT GGT TT/-3'.

CRO with thiol link at 5':
5'-/5ThioMC6-D/TTT TTT CCT CCT CCT CCT TCT

CCT CCT CCT CCT TT/-3'.

AS1411 with thiol link at 5' and
fluorophore Cy5 at 3':
5'-/5ThioMC6-D/TTT TTT GGT GGT GGT GGT TGT GGT GGT GGT GGT TT/Cy5Sp/-3'.
```

CRO with thiol link at 5' fluorophore Cy5 at 3':
5'-/5ThioMC6-D/TTT TTT CCT CCT CCT CCT TCT CCT CCT CCT CCT TT/Cy5Sp/-3'.

The thiol ends of aptamers was reduced by tri(2-carboxyethyl) phosphine TECP (50 mM) which is active in slightly acidic pH 6.5 of Tris-EDTA (10 mM) solution for 4-8 hours at room temperature. The solution of aptamers and TECP was purified using NAP-columns sephadex G-25. Accurate Spherical Gold nanoparticles 5 nm was purchased from NANOPARTZ and/or TED PELLA INC. The gold nanoparticles were filtered using 0.5 micron syringe filter. Gold nanoparticles and aptamers were mixed in the molar ratio of 1:40 in 25 ml RNAse and DNAse free water at room temperature overnight. Excess reagents were then removed by centrifugation at 15000 rpm for 20 min, followed by 3× wash with RNAse and DNAse free water and centrifugation to remove any unbound aptamers. To quantify the amount of aptamers conjugated on the nanoparticles surface, the aptamer conjugated GNP was incubated in 0.1M DTT at room temperature followed by the separation from the GNP by centrifugation. The supernatant was diluted and measured either spectrophotometically (A260 nm), then calculating the concentration from the aptamers standard dilution curve or by NanoDrop 2000 UV-VIS spectrophotometer. Similarly, the concentration of gold nanoparticles was calculated using spectrophotometric optical density (OD) at 511 nm and plotting the standard dilution curve to extrapolate the concentration of gold nanoparticles and the standard data provided by vendors.

In Vivo Efficacy of AS1411-GNPs

Figure 1B:
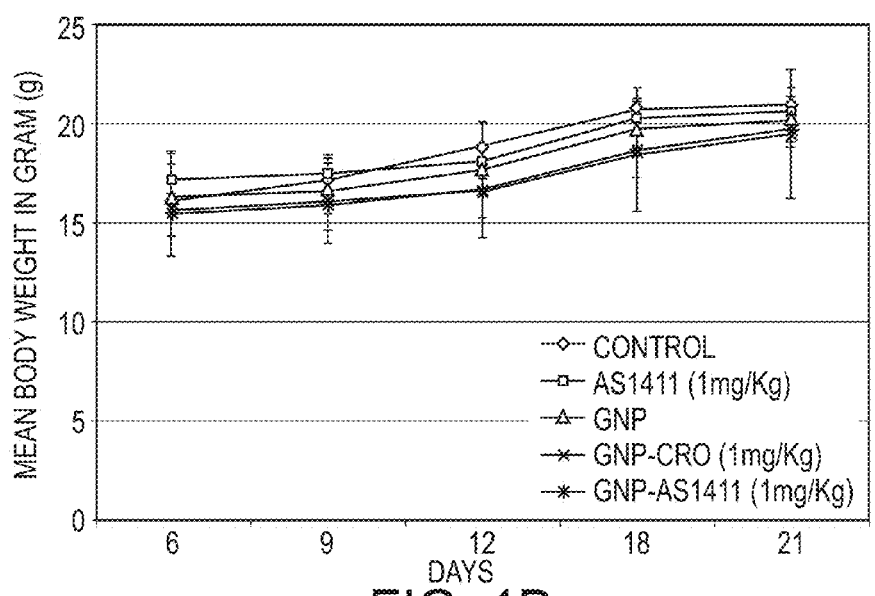
FIG. 1B is a graph of the mean body weight of the same mice during the treatment.

BALB/c nu/nu female mice (Harlan Laboratories Inc, IN, USA) were purchased and housed in University of Louisville animal care facility under pathogen free conditions. After one week acclimatization, mice were injected subcutaneously in each flank with 5×106 MDA-MB-231 cells in PBS. When the tumors were palpable (6 days), mice were randomized into five groups with five mice in each group as shown in Table 3. Mice then received daily intraperitoneal (i.p.) injection for 12 days. The weight and tumor volume was measured with digital vernier calipers (Fisher Scientific) twice a week and tumor volume was calculated using the formula ½ (width2×height) [17, 18]. Statistical analysis was performed using Sigma Stat 10, to determine the statistical significance by using standard student t-test. Treatment with AS1411 (1 mg/kg of aptamer) reduced tumor growth to 75% of vehicle-treated tumors (p<0.005) and GNP-AS1411 (equivalent to 1 mg/kg of aptamer) reduced growth to 94% of control tumors (p<0.005), whereas GNP and GNP-CRO (control aptamers) had only a modest effect on tumor growth (FIG. 1A). There were no significant changes in body weights of mice in any group (FIG. 1B).

TABLE 3

Treatment Groups

| Group | Number | Dose* |
|---|---|---|
| Vehicle only | 5 | 0 |
| AS1411 | 5 | 1 mg/kg |
| GNP | 5 | 200 pg/kg |
| GNP-CRO | 5 | 1 mg/kg |
| GNP-AS1411 | 5 | 1 mg/kg |

*equivalent aptamer concentration

GNP indicates the group treated with 200 picograms/kg of unconjugated gold nanoparticles (GNP); CRO-GNP indicates the group treated with 10 mg/kg of a control oligonucleotide-conjugated GNP, based on the amount of oligonucleotide only; AS1411 indicates the group treated with 10 mg/kg of AS1411 (GRO26B; unconjugated nucleotide having SEQ ID NO. 10); AS1411-GNP indicates the group treated with 1 mg/kg of a AS1411-conjugated GNP, based on the amount of oligonucleotide only; and Non Treated indicates the group which was not treated. The values in the lower left corner are relative p-values determined using the T-test; values below 0.05 indicate a statistically significant difference between the groups. The single p-value greater than 0.05, GNP vs. AS1411, indicated that there was no statistically significant difference between these two groups (likely due to the small sample sizes use in this study).

Figure 2A:
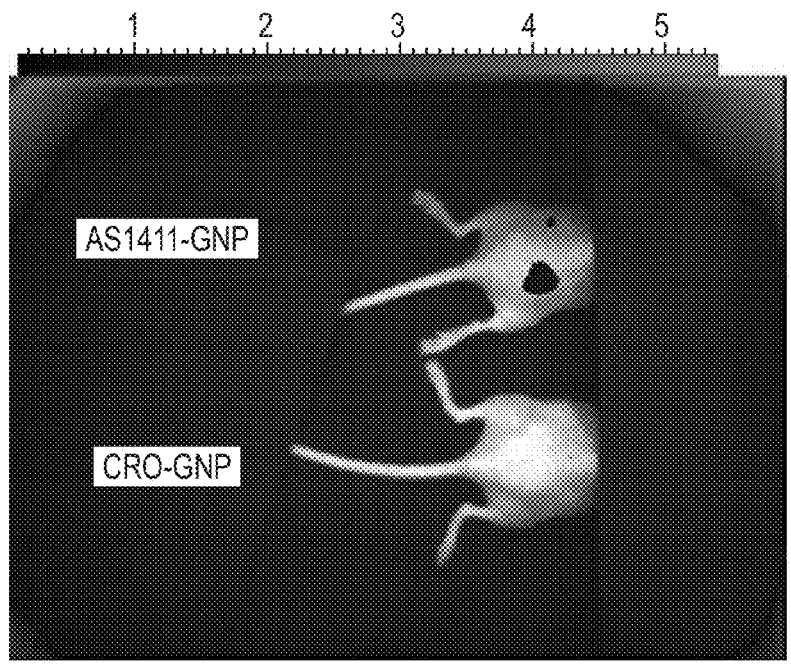
FIGS. 2A and 2B are images of two MDA231 xenograft mice injected retro-orbitally with about 200 ng/100 uL of AS1411-Cy5-GNP or CRO-Cy5-GNP. Image was acquired using a PHOTON IMAGER™ after 2 hrs (A) and 6 hrs (B) post injection.
Figure 2B:
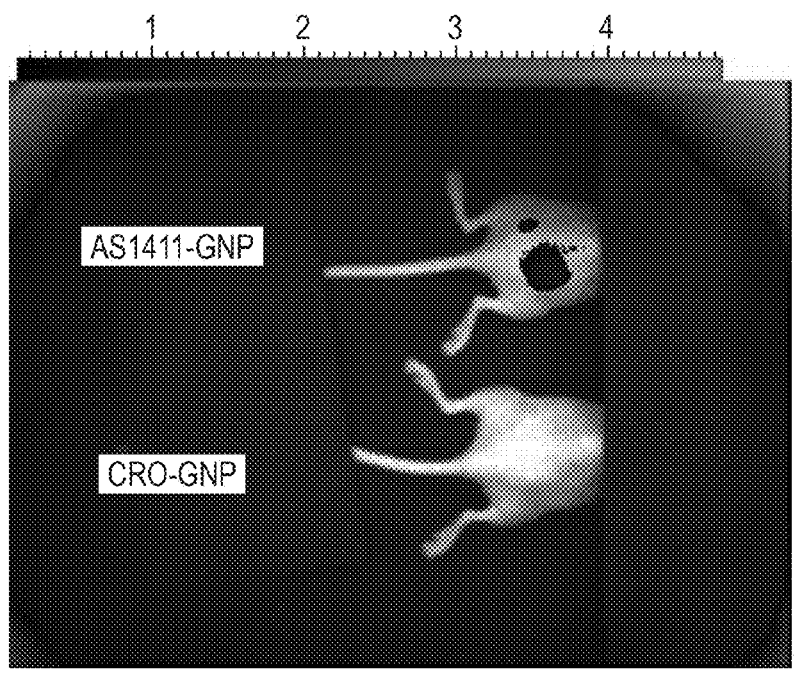

FIGS. 2A and 2B are images of two MDA231 xenograft mice (nude mice injected with MDA231 cancer cells), 2 hours (A) and 6 hours (B) after injection retro-orbitally with AS1411 conjugated with a fluorophor (cyanine dye Cy5) and gold nanoparticles (AS1411-Cy5-GNP), or with a control oligonucleotide conjugated with the fluorophor (cyanine dye Cy5) and gold nanoparticles (CRO-Cy5-GNP). The images were acquired using a PHOTON IMAGER™ at 680 nm. The images show that the tumors accumulate AS1411-Cy5-GNP, while CRO-Cy5-GNP is not accumulated.

AS1411-GNPs Tumor-Selective Antiproliferative Effects on Cells

Figure 3A:
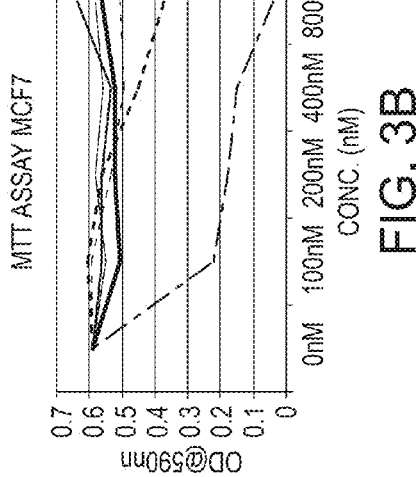
FIGS. 3A-D show the effect on cell proliferation of different concentrations of one of the composition indicated, or without treatment (NT), using an MTT assay. Cells were seeded in 96 well plate at density of 1000 cells/well. Cells were treated with the different concentration of AS1411 and AS1411-GNP for five days.
Figure 3B:
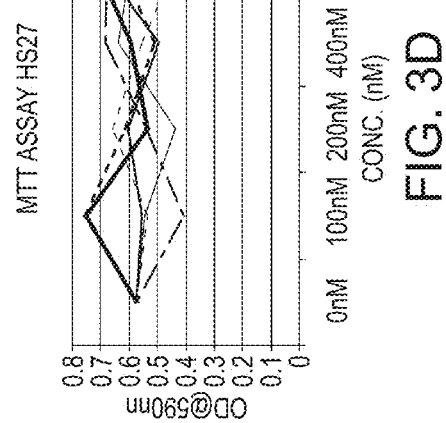
Figure 3C:
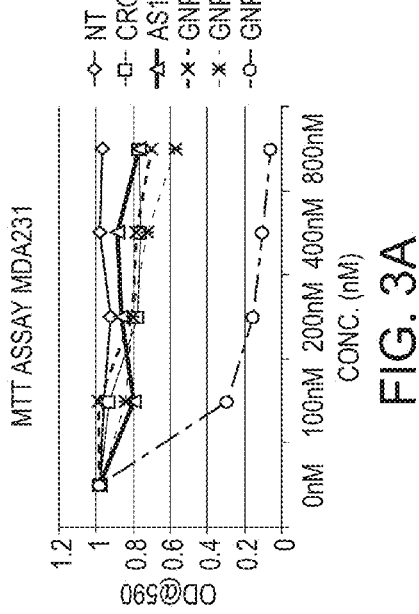
Figure 3D:
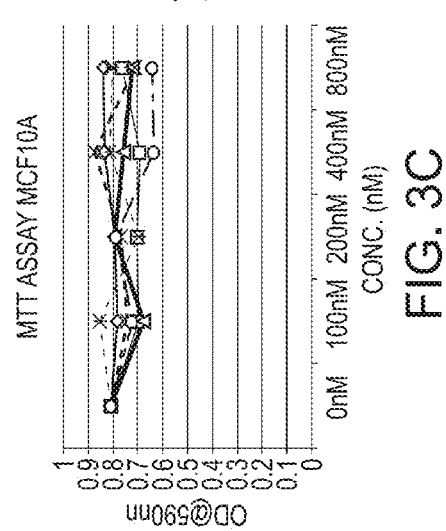

FIGS. 3A-D show the effect cell proliferation of different concentrations of one of the composition indicated, or without treatment (NT), using an MTT assay. Cells were seeded in 96 well plates at a density of 1000 cells/well, and treated for 5 days. GNP indicates the group treated with unconjugated gold nanoparticles; GNP-CR indicates the group treated a control oligonucleotide-conjugated GNP; AS1411 indicates the group treated with AS1411; GNP-AS indicates the group treated with AS1411-conjugated GNP. FIG. 3A shows the result of treatment of MDA231 cells (estrogen negative breast cancer cell line), FIG. 3B shows the result of treatment of MCF7 cells (estrogen dependent breast cancer cell line), FIG. 3C shows the result of treatment of MCF10A cells (human epithelial cell line) and FIG. 3D shows the result of treatment of Hs27 cells (human fibroblast cell line).

Figure 4A:
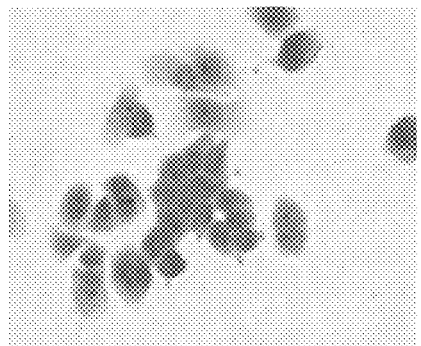
FIGS. 4A-D are optical micrographs of MCF7 cells treated by silver enhancement staining for gold nanoparticles, illustrating comparative accumulation of gold nanoparticles after administration of the indicated composition, or without administration.
Figure 4B:
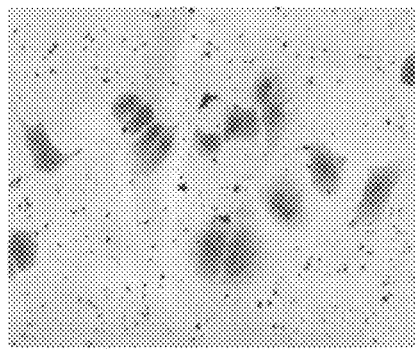
Figure 4C:
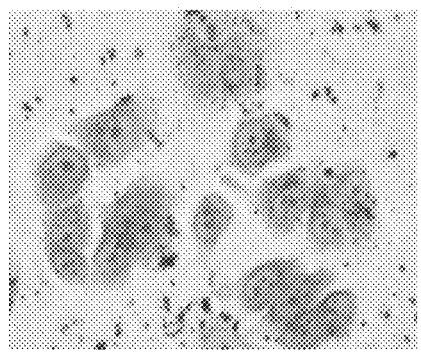
Figure 4D:

FIGS. 4A-D are optical micrographs of MCF7 cells treated by silver enhancement staining for gold nanoparticles, illustrating comparative accumulation of gold nanoparticles after administration of the indicated composition, or without administration. As shown, no significant accumulation occurs after administration of unconjugated gold nanoparticles (FIG. 4B), and only slight accumulation occurs after administration of control oligonucleotide-conjugated gold particles (FIG. 4C). Administration of AS1411-conjugated gold nanoparticles, however, results in significant accumulation of gold nanoparticles, as indicated by the arrows (FIG. 4D). Non-treated cells are also shown (FIG. 4A).

Figure 5:
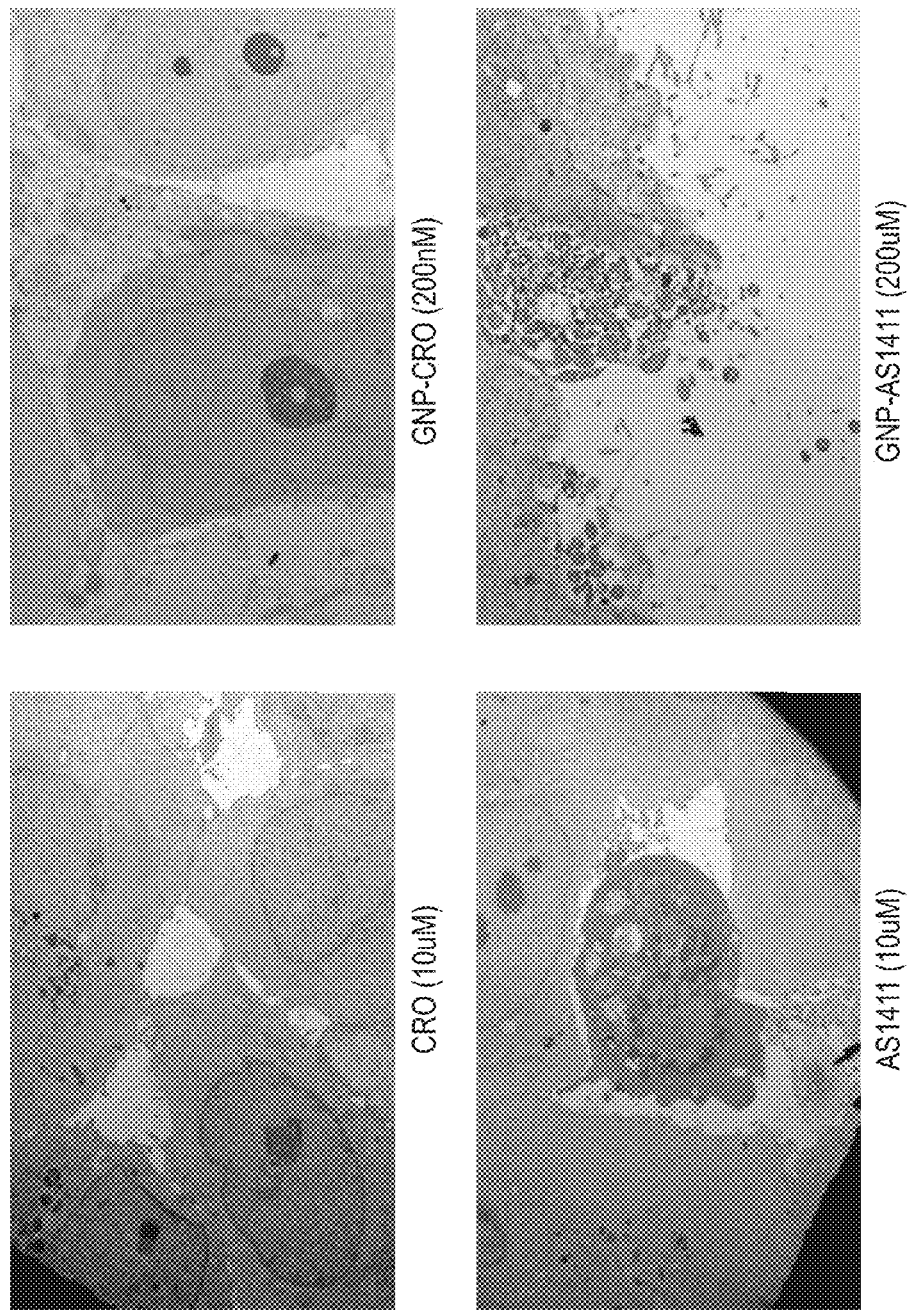
FIG. 5 is electron micrographs of MDA231 cells after administration of a control oligonucleotide (FIG. 5A) or control oligonucleotide-conjugated gold particles (FIG. 5B), or AS1411 (FIG. 5C), or AS1411-conjugated gold nanoparticles (FIG. 5D).

AS1411-GNPs were synthesized for treating cancer and for cancer imaging. Studies to assess the anticancer activity of AS1411 linked to 5 nm gold nanoparticles indicated that the conjugates had greatly enhanced antiproliferative effects on breast cancer cells compared to AS1411 alone. Microscopic examination revealed increased uptake in breast cancer cells for GNP-AS1411 compared to GNP alone or GNP conjugated to a control oligonucleotide. FIG. 5 is electron micrographs of MDA231 cells after administration of the indicated composition. As shown, no significant effect occurs after administration of a control oligonucleotide or control oligonucleotide-conjugated gold particles. The initial stages of apoptosis are apparent after administration of AS1411. Administration of AS1411-conjugated gold nanoparticles, however, results in formation of vacuoles and what appear to be apoptotic bodies, indicating that the cells are dying off in an apoptosis-like process.

Administration of GNP-AS1411 induced breast cancer cell vacuolization and death, similar to that seen at higher concentrations of AS1411. The GI50 for AS1411 conjugated GNP against breast cancer cells were in the 50-250 nM range, compared to 1-10 uM range for unconjugated AS1411 (equivalent aptamer concentration). Preliminary studies indicated that these AS1411-GNPs had selective uptake in tumor tissue following systemic administration in mice. Moreover, AS1411-GNPs retained the cancer-selectivity of AS1411 and had no effect on non-malignant cells.

Figure 6A:
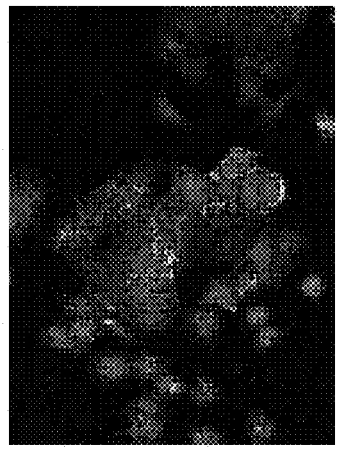
FIGS. 6A-D are confocal microscope images of MCF7 cells after administration of a control oligonucleotide (FIG. 6A) or control oligonucleotide-conjugated gold particles (FIG. 6C), or AS1411 (FIG. 6B), or AS1411-conjugated gold nanoparticles (FIG. 6D).
Figure 6B:
Figure 6C:
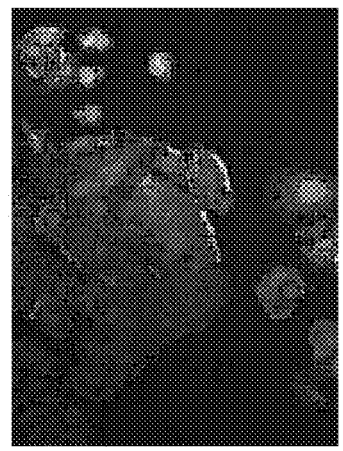
Figure 6D:
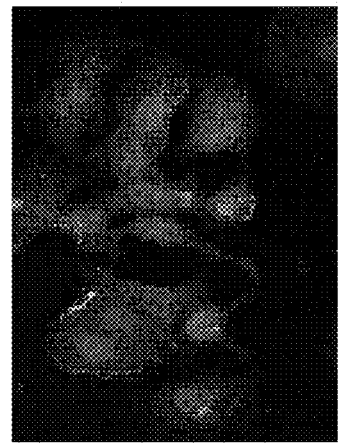

FIGS. 6A-D are confocal microscope images of MCF7 cells after administration of the indicated composition; different shading indicates cell membranes and gold nanoparticles. As shown, no significant effect occurs after administration of a control oligonucleotide (FIG. 6A) or control oligonucleotide-conjugated gold particles (FIG. 6C). The initial stages of apoptosis are apparent after administration of AS1411 (FIG. 6B). Administration of AS1411-conjugated gold nanoparticles, however, show a dramatic enlargement of the cells (FIG. 6D).

Figure 7:
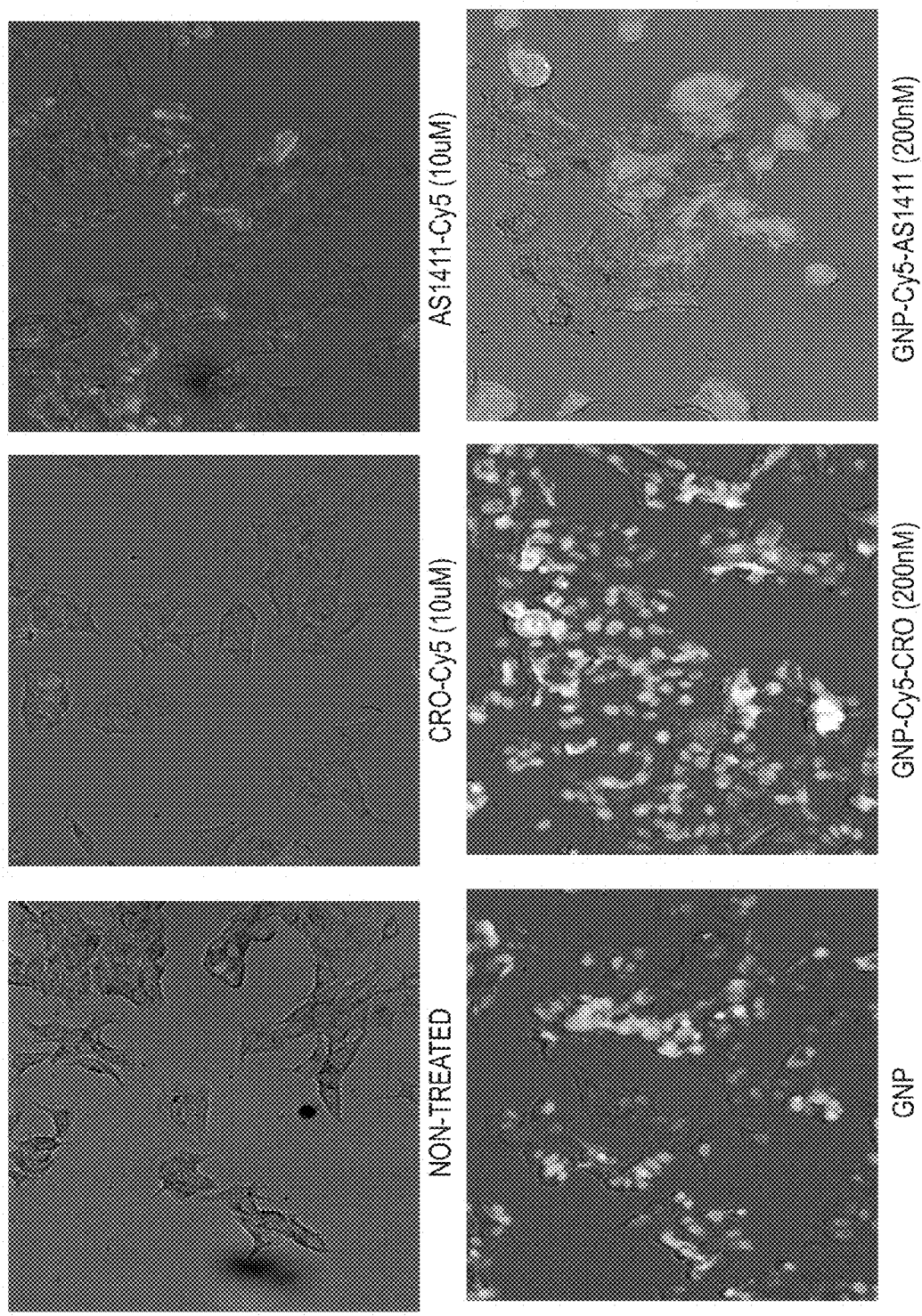
FIG. 7 is fluorescent microscopy images of MCF7 cells after 5 days of administration of a control oligonucleotide, AS1411-Cy5, unconjugated GNP, control oligonucleotide-conjugated gold particles, AS1411-Cy5 conjugated gold nanoparticles and non-treated cells.

FIG. 7 is fluorescent microscopy images of MCF7 cells after 5 days of administration of the indicated composition; different shading indicates cell membranes and gold nanoparticles. As shown, no significant effect occurs after administration of a control oligonucleotide, unconjugated GNP or control oligonucleotide-conjugated gold particles. The initial stages of apoptosis are apparent after administration of AS1411-Cy5. Administration of AS1411-Cy5 conjugated gold nanoparticles, however, show a dramatic enlargement of the cells and accumulation of GNP. Non-treated cells are also shown.

Figure 8:
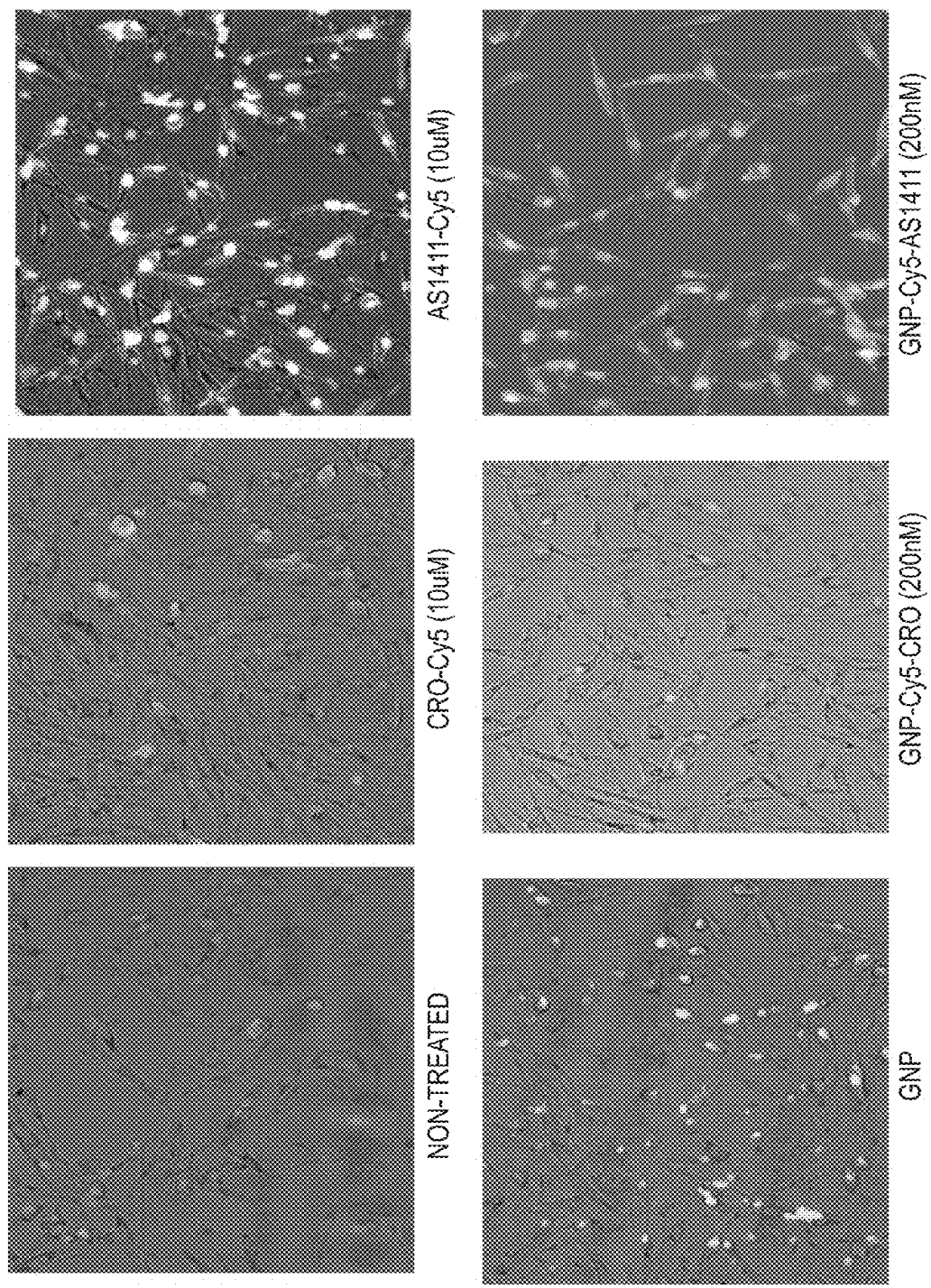
FIG. 8 is fluorescent microscopy images of MDA231 cells after 5 days of administration of a control oligonucleotide, unconjugated GNP, control oligonucleotide-conjugated gold particles, AS1411-Cy5, AS1411-Cy5 conjugated gold nanoparticles and non-treated cells.

FIG. 8 is fluorescent microscopy images of MDA231 cells after 5 days of administration of the indicated composition; different shading indicates cell membranes and gold nanoparticles. As shown, no significant effect occurs after administration of a control oligonucleotide, unconjugated GNP or control oligonucleotide-conjugated gold particles. The initial stages of apoptosis are apparent after administration of AS1411-Cy5. Administration of AS1411-Cy5 conjugated gold nanoparticles, however, show a dramatic enlargement of the cells and accumulation of GNP. Non-treated cells are also shown.

Comparison of Different Routes of Injection for Delivery of AS1411-GNP to Target Tissue Three different routes of injection for delivery of GNP-AS1411 to target tissue were tested: intraperitoneal, intravenous, via tail vein, retro-orbital, injection. Based on pilot studies, it was determined that for long term and repeated injections (as in therapeutic dosing), intraperitoneal injection was preferred for its convenience and because the slower biodistribution (compared to intravenous or retro-orbital) was not a concern. For imaging, either tail vein or retro-orbital injections were used because it delivered the drug directly into the blood, resulting in more rapid systemic distribution and avoiding residual signal in the peritoneum that was observed when delivering through the intraperitoneal route. Pilot in vivo studies in mice with breast cancer cell line MDA-MB-231 xenografts have shown that intravenous administration of AS1411-GNPs at 1 mg/kg/day for 14 days could almost completely inhibit tumor growth. These tumor growth inhibitory activities were aptamer-related because GNPs conjugated to control DNA had little or no activity, in terms of internalization in breast cancer cells, uptake in xenografts, and inhibitory effects on breast cancer cells growing in culture or in vivo.

Effect of GNP Size and Linkers Length on Cell Proliferation

Syntheses and analyses of GNPs and linkers were performed as follows: colloid spherical gold nanoparticles of different size (5, 10, 15 nm) were purchased from Ted Pella Inc. (Redding, Calif.) and Nanopartz (Loveland, Colo.). Size analyses of these gold nanoparticles were confirmed using PARTICLES SIZE ANALYZER 90 PLUS (Brookhaven Instrument), and the sizes of gold nanoparticles were within the ranges as described by the manufacturers. Fluorophore (Cy5)-linked oligonucleotides (AS1411 and CRO), with or without carbon spacers and thiol groups, were purchased from Integrated DNA Technologies (San Diego, Calif.). Cy5, or cyanine-5 phosphoramidite (1-[3-(4-monomethoxytrityloxy)propyl]-1'-[3-[(2-cyanoethyl)-(N,N-diisopropyl)phosphoramidityl]propyl]-3,3,3',3'-tetramethyl-indodicarbocyanine chloride) has the structure shown in Formula I:

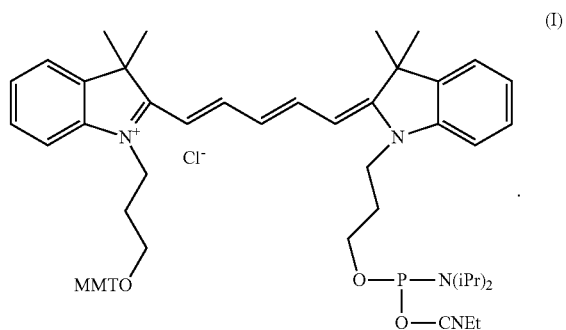

The linkers, C3-thiol (1-O-dimethoxytrityl-propyl-disulfide, 1'-succinyl-lcaa), MC6-D/iSP-9 (9-O-dimethoxytrityl-triethylene glycol, 1-[(2-cyanoethyl)-(N,N-diisopropyl)]), and MC6-D/iSP-18(18-O-dimethoxytritylhexaethylene glycol, 1-[(2-cyanoethyl)-(N,N-diisopropyl)]), have the structures shown in Formulas II, III and IV, respectively:

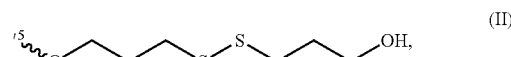
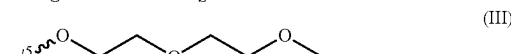
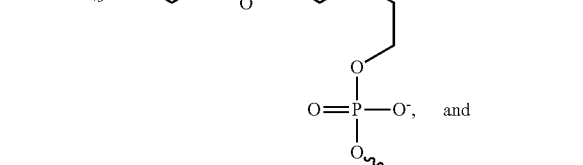
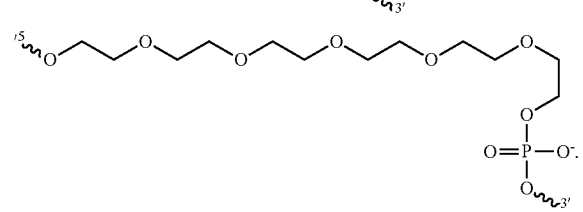

Figure 9A:
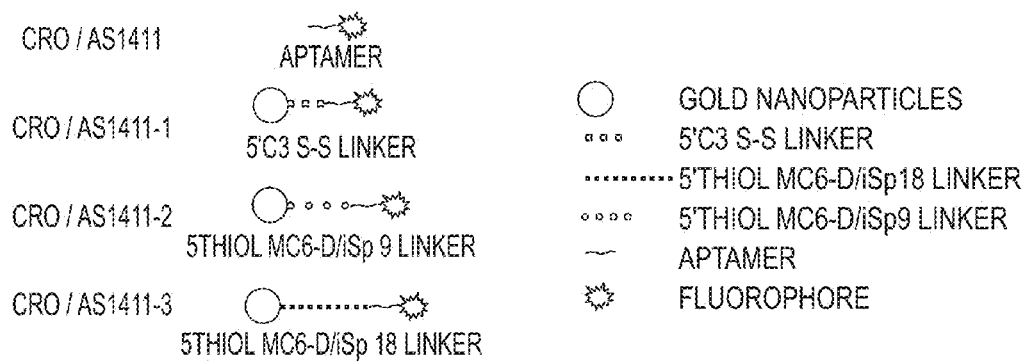
FIG. 9A is a sketch of different linkers used to conjugate AS1411/CRO to gold nanoparticles.
Figure 9B:
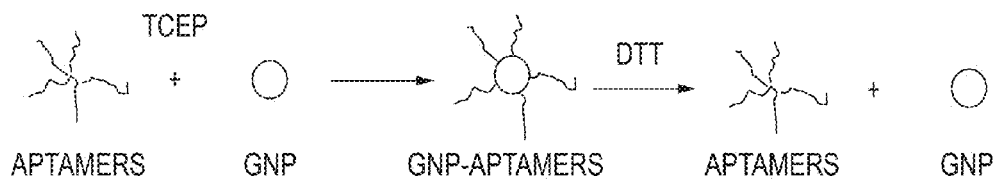
FIG. 9B is a sketch of attaching and detaching aptamers to gold nanoparticles.
Figure 10:
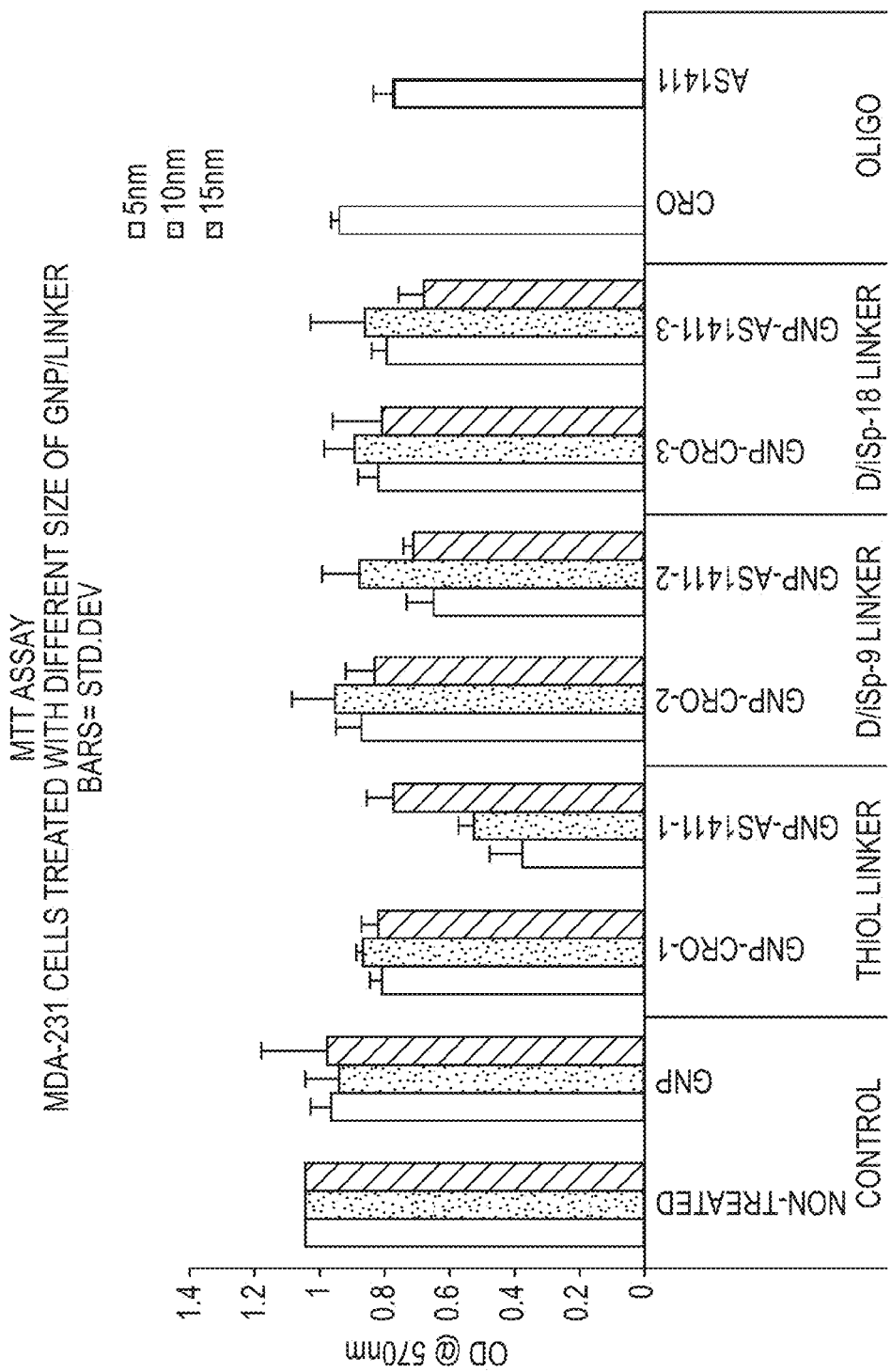
FIG. 10 shows the result of a cell proliferation/cytotoxicity (MTT) assay: MDA-231 cells were treated with the various agents for 72 hours at 200 nM equivalent aptamer concentration. For comparison, AS1411 and CRO alone were used at a concentration of 10 µM.
Figure 11A:
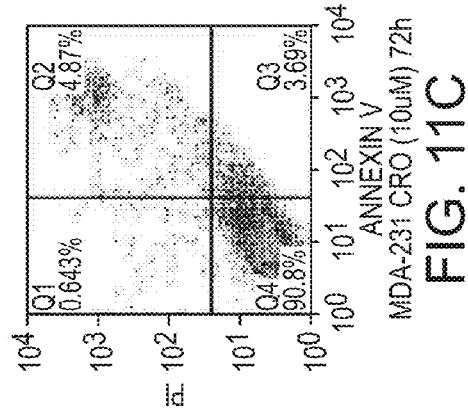
FIGS. 11A-G are graphs of flow cytometric assays of MDA-231 cells stained with both PI and Annexin V: (A) cells not treated (control sample); (B) cells treated with AS1411 (at a concentration of 10 µM) for 72 hours; (C) cells treated with CRO control oligonucleotide; (D) cells treated with unconjugated gold nanoparticles; (E) cells treated with GNP-AS1411 (at 200 nM equivalent aptamer concentration); (F) cells treated with the control GNP-CRO (at 200 nM equivalent aptamer concentration); (G) positive control cells treated with camptothecin (at a concentration of 6 ug/ml for 20 hours).
Figure 11B:
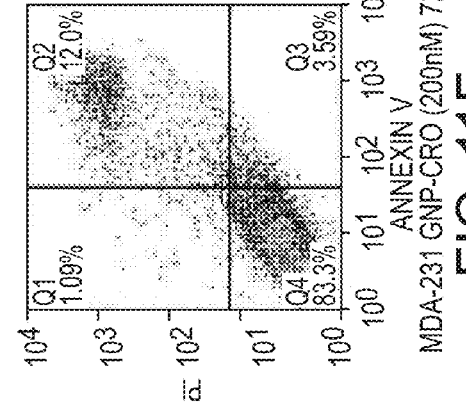
Figure 11C:
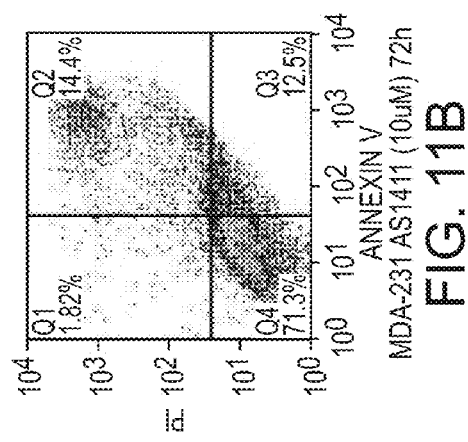
Figure 11D:
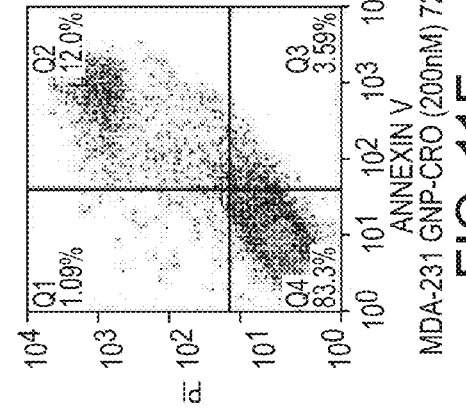
Figure 11E:
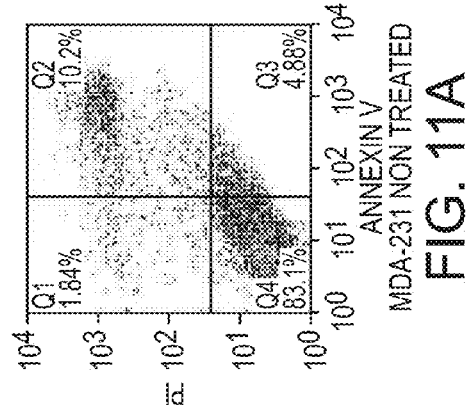
Figure 11F:
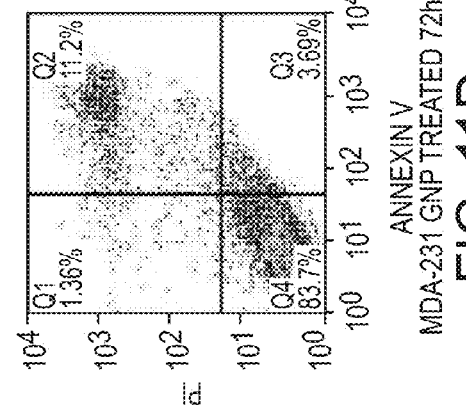
Figure 11G:
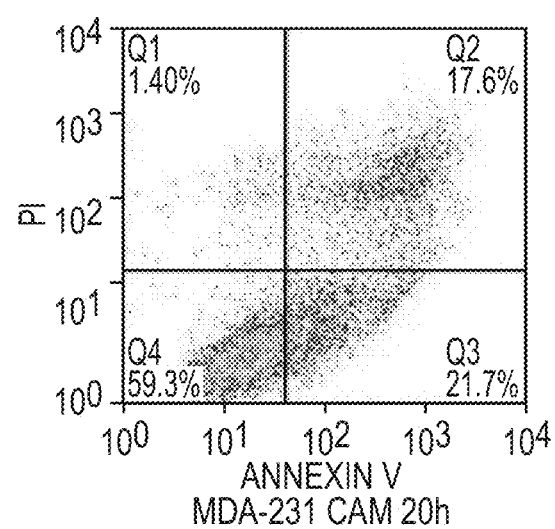

FIG. 9A is a cartoon representation of the various agents tested. FIG. 9B is an illustration of the reaction to form conjugates, and to separate the parts of the conjugates. A cell proliferation/cytotoxicity assay (MTT) was performed by treating MDA-231 cells with different sizes of gold nanoparticles (5, 10, 15 nm) and three different linker lengths (C3-thiol, MC6-D/iSP-9, and MC6-D/iSP-18) for 72 hours at concentrations equivalent to 200 nM oligonucleotide. The optimal size and composition for GNP-AS1411 particles was determined in terms of their antiproliferative activity against breast cancer cells. The most profound effects on the cell proliferation occurred using GNP-AS1411 of average diameter 5 nm with C3 thiol linker (64% inhibition), followed by 10 nm with C3 thiol linker (50% inhibition) (FIG. 10 and Table 4).

TABLE 4

Percent cell growth after treatment with GNP-AS1411, with different GNP sizes and linker length for 72 hours.

| GNP size | Non-treated (control) | GNP only | C3-thiol | MC6-D/iSP-9 | MC6-D/iSP-18 |
|---|---|---|---|---|---|
| 5 nm | 100 | 92 | 36 | 61 | 78 |
| 10 nm | 100 | 90 | 50 | 84 | 83 |
| 15 nm | 100 | 93 | 74 | 68 | 65 |

Gold Nanoparticles (5 nm) Conjugated AS1411 (GNP-AS1411) Cause Late Apoptosis/Necrosis of MDA-MB-231 Breast Cancer Cells The extent and mechanism of cell death induced by the active GNP-AS1411 was investigated by flow cytometry (FIGS. 11A-G). Flow cytometric analysis of MDA-MB-231 cells stained with FITC-Annexin V and propodium iodide (PI) showed that GNP-AS1411 could potently and specifically induce cell death in breast cancer cells. Flow cytometric assays were performed using FITC Annexin V Apoptosis Detection Kit (BD Bioscience) and data analysis was performed using FLOW JO software (ver. 7.6.5). MDA-MB-231 cells (5×104) were plated in T-25 flask in complete medium and treated as indicated. Staining identified cells that were viable (negative for both PI and Annexin V), early apoptotic (positive for Annexin v, but negative for PI), and late apoptotic or necrotic cells (positive for both PI and Annexin V). (A) In the MDA-MB-231 non-treated control sample, the majority of cells (83%) were viable. (B) In cells treated with AS1411 (10 μM) for 72 hours, there was a decrease in the viable population and an increase in the early apoptotic (12%) and late apoptotic/necrotic population (14%). (C) Cells treated with CRO control oligonucleotides showed a mostly viable population of cells (90%), similar to untreated control. (D) Cells treated with unconjugated gold nanoparticles showed most of the cells were viable (83%). (E) MDA-MB-231 cells treated with GNP-AS1411 (200 nM equivalent aptamer concentration) had a greatly increased population of cells positive for annexin V and/or PI, with most (71%) showing evidence of late apoptosis or necrosis. (F) Cells treated with the control GNP-CRO (200 nM equivalent aptamer concentration) showed comparable results with untreated and GNP-treated controls. The positive control (G) were the cells treated with camptothecin (6 ug/ml for 20 hours) to show the Annexin V and PI positive cells indicative of apoptosis (21%) and late apoptotic (17%) cells.

In Vivo Biodistribution of AS1411-GNP Conjugated to Fluorophore Cy5

Figure 12:
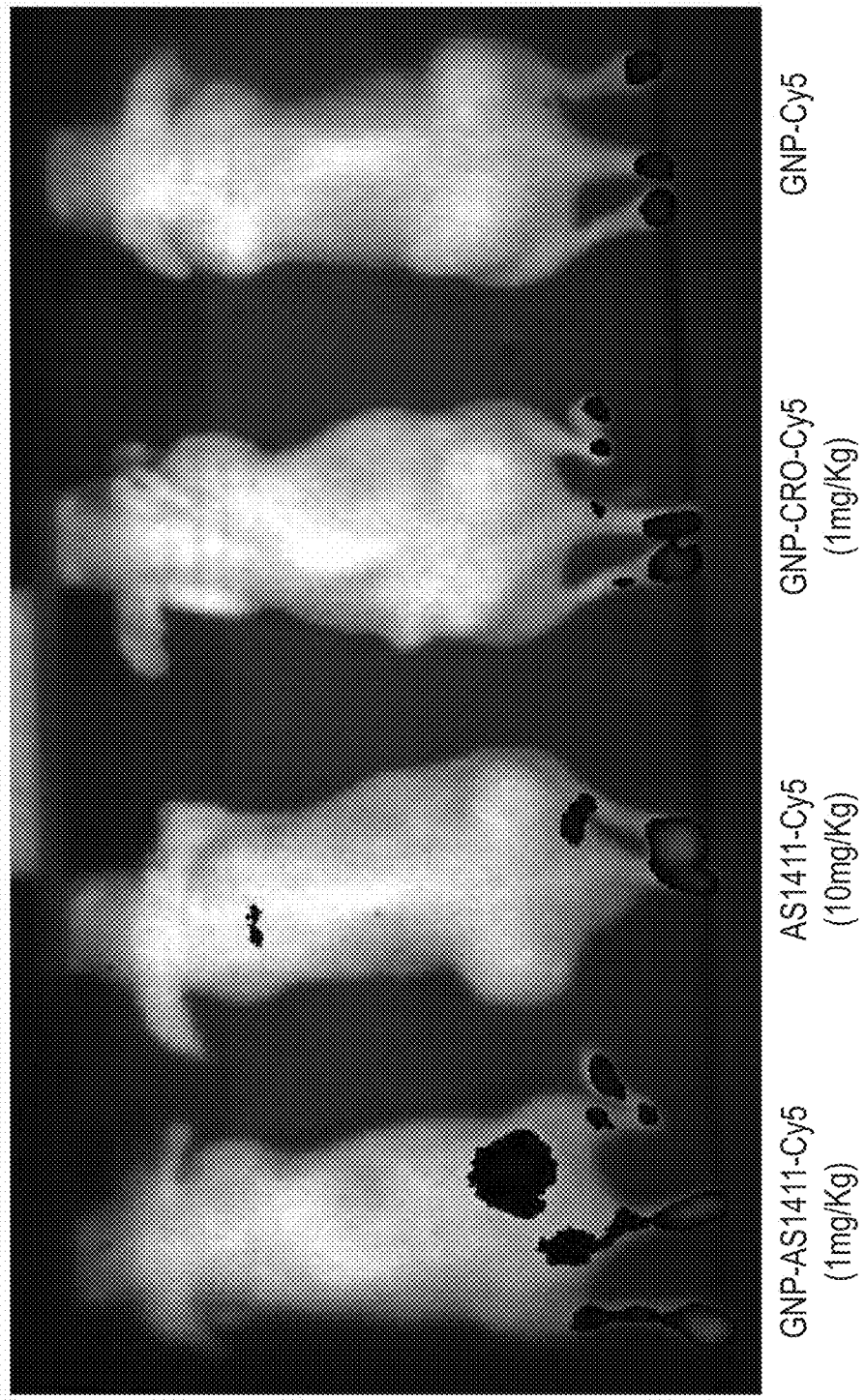
FIG. 12 shows images of mice treated by intraperitoneal injection with GNP-AS1411-Cy5 (1 mg/kg equivalent aptamer concentration), AS1411-Cy5 (10 mg/Kg) and GNP-CRO-Cy5 (1 mg/kg equivalent aptamer concentration), and GNP-Cy5, and imaged after 96 hours.
Figure 13A:
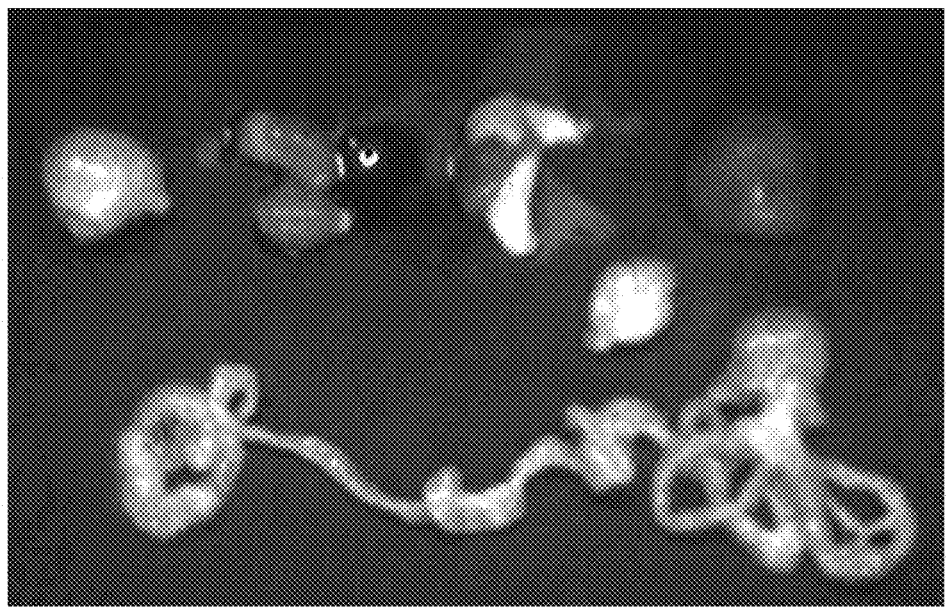
FIGS. 13A and B show the biodistribution of AS1411-GNP-Cy5: the mice were treated, euthanized and organs were photographed (A) and examined for fluorescence (B).
Figure 13B:
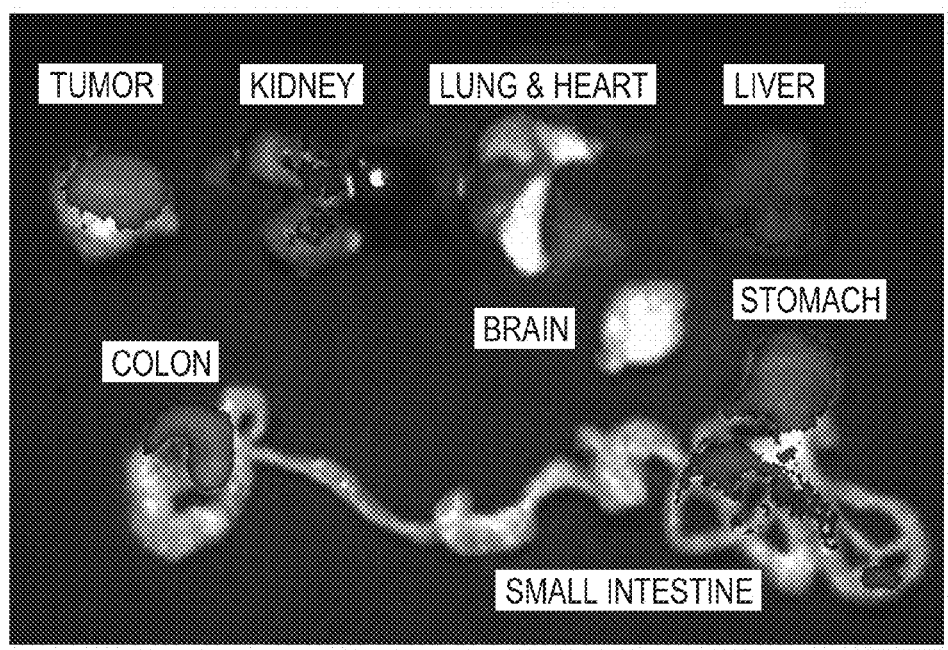

The use of multimodal imaging approaches utilizing optical and microCT was useful for detection of primary or disseminated breast cancer tumors. In this experiment a Cy5 fluorophore was linked to the 5'-end of AS1411 and conjugated to the GNP (to give GNP-AS1411-Cy5), in order to evaluate its utility as a complex not only for optical imaging but also as a contrast agent for computed tomography (CT). A similar construct with CRO was synthesized as a control. Nude mice with MDA-MB-231 breast cancer xenografts on each flank were administered a single injection of fluorophore-oligonucleotide-GNP. Images were acquired using IVIS Imaging System/MAESTRO Fluorescence Imaging and preliminary data showed that GNP-AS1411-Cy5 (1 mg/kg) concentration in the tumor is many times more than that using AS1411-Cy5 without GNP (10 mg/kg), or GNP-CRO-Cy5 (FIG. 12). It was noted that all mice exhibited strong signals on their extremities (legs and paws) and tails; these were artifacts from the urine and feces of the mice in cage where they were housed (possibly due to a fluorescent substance in the animal feed). Washing the mice and housing them in new clean new cages before imaging can prevent this problem. Biodistribution analysis also confirmed that, besides liver, kidney and intestine, most of the GNP-AS1411 accumulated in the tumor (FIG. 13). This is a proof of concept that conjugating AS1411 to gold nanoparticles can specifically target the tumors. Mice were treated by intraperitoneal injection with the indicated substances and were imaged after 96 h. Images showed high accumulation of GNP-AS1411-Cy5 (1 mg/kg aptamer concentration) in breast cancer xenograft, as compared to AS1411 (10 mg/Kg) and GNP-CRO alone.

REFERENCES

[1] Stedman, T. L. 2000. Stedman's medical dictionary. Lippincott Williams & Wilkins, Philadelphia. xxxvi, [127], 2098.

[2] Miller, D., P. Bates, and J. Trent. 2000. Antiproliferative activity of G-rich oligonucleotides and method of using same to bind to nucleolin, Int'l Pub. No. WO 00/61597.

[3] Bates P J, Miller D M, Trent J O, Xu X, "A New Method for the Diagnosis and Prognosis of Malignant Diseases" International Application, Int'l Pub. No. WO 03/086174 A2 (23 Oct. 2003).

[4] Bates P J, Miller D M, Trent J O, Xu X, "Method for the Diagnosis and Prognosis of Malignant Diseases" U.S. Patent App. Pub., Pub. No. US 2005/0053607 A1 (10 Mar. 2005).

[5] Derenzini M, Sirri V, Trere D, Ochs R L, "The Quantity of Nucleolar Proteins Nucleolin and Protein B23 is Related to Cell Doubling Time in Human Cancer Cells" Lab. Invest. 73:497-502 (1995).

[6] Bates P J, Kahlon J B, Thomas S D, Trent J O, Miller D M, "Antiproliferative Activity of G-rich Oligonucleotides Correlates with Protein Binding" J. Biol. Chem. 274: 26369-77 (1999).

[7] Miller D M, Bates P J, Trent J O, Xu X, "Method for the Diagnosis and Prognosis of Malignant Diseases" U.S. Patent App. Pub., Pub. No. US 2003/0194754 A1 (16 Oct. 2003).

[8] Bandman O, Yue H, Corley N C, Shah P, "Human Nucleolin-like Protein" U.S. Pat. No. 5,932,475 (3 Aug. 1999).

[9] Reyes-Reyes E M, Teng Y, Bates P J, "A New Paradigm for Aptamer Therapeutic AS1411 Action: Uptake by Macropinocytosis and Its Stimulation by a Nucleolin-Deoendnet Mechanism" Cancer Res 70(21): 8617-29 (2010).

[10] Huang Y, Shi H, Zhou H, Song X, Yuan S, Luo Y, "The Angiogenic Function of Nucleolin is Mediated by Vascular Endothelial Growth Factor and Nonmuscle Myosin" Blood 107(9): 3564-71 (2006).

[11] Jain, K. K., *Advances in the field of nanooncology*. BMC medicine, 2010. 8: p. 83.
[12] Portney, N. G. and M. Ozkan, *Nano-oncology: drug delivery, imaging, and sensing*. Analytical and bioanalytical chemistry, 2006. 384(3): p. 620-30.
[13] Bates, P. J., E. W. Choi, and L. V. Nayak, *G-rich oligonucleotides for cancer treatment*. Methods in molecular biology, 2009. 542: p. 379-92.
[14] Bates, P. J., et al., *Discovery and development of the G-rich oligonucleotide AS1411 as a novel treatment for cancer*. Experimental and molecular pathology, 2009. 86(3): p. 151-64.
[15] Soundararajan, S., et al., *The nucleolin targeting aptamer AS1411 destabilizes Bcl-2 messenger RNA in human breast cancer cells*. Cancer research, 2008. 68(7): p. 2358-65.
[16] Javier, D. J., et al., *Aptamer-targeted gold nanoparticles as molecular-specific contrast agents for reflectance imaging*. Bioconjugate chemistry, 2008. 19(6): p. 1309-12.
[17] Euhus, D. M., et al., *Tumor measurement in the nude mouse*. Journal of surgical oncology, 1986. 31(4): p. 229-34.
[18] Tomayko, M. M. and C. P. Reynolds, *Determination of subcutaneous tumor size in athymic (nude) mice*. Cancer chemotherapy and pharmacology, 1989. 24(3): p. 148-54.
[19] Girvan, A. C., et al., *AGRO100 inhibits activation of nuclear factor-kappaB (NF-kappaB) by forming a complex with NF-kappaB essential modulator (NEMO) and nucleolin*. Molecular cancer therapeutics, 2006. 5(7): p. 1790-9.
[20] Mosmann, T., *Rapid colorimetric assay for cellular growth and survival: application to proliferation and cytotoxicity assays*. Journal of immunological methods, 1983. 65(1-2): p. 55-63.
[21] Vermes, I., et al., *A novel assay for apoptosis. Flow cytometric detection of phosphatidylserine expression on early apoptotic cells using fluorescein labelled Annexin V*. Journal of immunological methods, 1995. 184(1): p. 39-51.
[22] Sprague, J. E., et al., *Noninvasive imaging of osteoclasts in parathyroid hormone-induced osteolysis using a 64Cu labeled RGD peptide*. Journal of nuclear medicine: official publication, Society of Nuclear Medicine, 2007. 48(2): p. 311-8.
[23] Morgan D. M., *Methods Mol. Biol.* 1998. 79:179-183.
[24] Zhang, Y. et al., *A surface-charge study on cellular-uptake behavior of F3-peptide-conjugated iron oxide nanoparticles*. Small, 2009 5(17): p. 1990-6.
[25] Orringer, D. A., et al. *In vitro characterization of a targeted, dye-loaded nanodevice for intraoperative tumor delineation*. Neurosurgery, 2009 64(5): p. 965-72.

---

What is claimed is:

1. A composition, comprising an anti-nucleolin agent conjugated to nanoparticles,
   wherein the nanoparticles comprise gold
   and wherein the anti-nucleolin agent is AS1411 (SEQ ID NO: 10).

2. The composition of claim 1, further comprising a cyanine dye.

3. The composition of claim 1, wherein the nanoparticles have an average diameter of 1 to 50 nm.

4. The composition of claim 1, wherein the nanoparticles have an average diameter of 1 to 20 nm.

5. A pharmaceutical composition, comprising the composition of claim 1 and a pharmaceutically acceptable carrier.

6. A method of treating cancer, comprising administering an effective amount of the pharmaceutical composition of claim 5, to a patient in need thereof.

7. The method of claim 6, wherein the cancer is selected from the group consisting of melanoma, lymphoma, plasmocytoma, sarcoma, glioma, thymoma, leukemia, breast cancer, prostate cancer, colon cancer, liver cancer, esophageal cancer, brain cancer, lung cancer, ovary cancer, endometrial cancer, bladder cancer, kidney cancer, cervical cancer and hepatoma.

8. The method of claim 7, wherein the cancer is selected from the group consisting of breast cancer, prostate cancer, colon cancer and lung cancer.

9. The method of claim 6, further comprising administering a second cancer treatment selected from the group consisting of vinorelbine, mytomycin, camptothecin, cyclyphosphamide, methotrexate, tamoxifen citrate, 5-fluorouracil, irinotecan, doxorubicin, flutamide, paclitaxel, docetaxel, vinblastine, imatinib mesylate, anthracycline, letrozole, arsenic trioxide, anastrozole, triptorelin pamoate, ozogamicin, irinotecan hydrochloride, BCG live, leuprolide acetate implant, bexarotene, exemestane, topotecan hydrochloride, gemcitabine HCL, daunorubicin hydrochloride, toremifene citrate, carboplatin, cisplatin, oxaliplatin and any other platinum-containing oncology drug, trastuzumab, lapatinib, gefitinb, cetuximab, panitumumab, temsirolimus, everolimus, vandetanib, vemurafenib, crizotinib, vorinostat, bevacizumab, radiation therapy, hyperthermia, gene therapy and photodynamic therapy.

10. A pharmaceutical composition, comprising the composition of claim 2 and a pharmaceutically acceptable carrier.

11. A pharmaceutical composition, comprising the composition of claim 3 and a pharmaceutically acceptable carrier.

12. A pharmaceutical composition, comprising the composition of claim 4 and a pharmaceutically acceptable carrier.

13. A method of treating cancer, comprising administering an effective amount of the pharmaceutical composition of claim 10, to a patient in need thereof.

14. A method of treating cancer, comprising administering an effective amount of the pharmaceutical composition of claim 11, to a patient in need thereof.

15. A method of treating cancer, comprising administering an effective amount of the pharmaceutical composition of claim 12, to a patient in need thereof.

16. The method of claim 15, wherein the cancer is selected from the group consisting of melanoma, lymphoma, plasmocytoma, sarcoma, glioma, thymoma, leukemia, breast cancer, prostate cancer, colon cancer, liver cancer, esophageal cancer, brain cancer, lung cancer, ovary cancer, endometrial cancer, bladder cancer, kidney cancer, cervical cancer and hepatoma.

17. The method of claim 16, wherein the cancer is selected from the group consisting of breast cancer, prostate cancer, colon cancer and lung cancer.

18. The method of claim 15, further comprising administering a second cancer treatment selected from the group consisting of vinorelbine, mytomycin, camptothecin, cyclyphosphamide, methotrexate, tamoxifen citrate, 5-fluorouracil, irinotecan, doxorubicin, flutamide, paclitaxel, docetaxel, vinblastine, imatinib mesylate, anthracycline, letrozole, arsenic trioxide, anastrozole, triptorelin pamoate, ozogamicin, irinotecan hydrochloride, BCG live, leuprolide acetate implant, bexarotene, exemestane, topotecan hydrochloride, gemcitabine HCL, daunorubicin hydrochloride, toremifene citrate, carboplatin, cisplatin, oxaliplatin and any other platinum-containing oncology drug, trastuzumab, lapatinib, gefitinb, cetuximab, panitumumab, temsirolimus, everolimus, vandetanib, vemurafenib, crizotinib, vorinostat, bevacizumab, radiation therapy, hyperthermia, gene therapy and photodynamic therapy.

19. The method of claim 14, wherein the cancer is selected from the group consisting of breast cancer, prostate cancer, colon cancer and lung cancer.

20. The method of claim 14, further comprising administering a second cancer treatment selected from the group consisting of vinorelbine, mytomycin, camptothecin, cyclyphosphamide, methotrexate, tamoxifen citrate, 5-fluorouracil, irinotecan, doxorubicin, flutamide, paclitaxel, docetaxel, vinblastine, imatinib mesylate, anthracycline, letrozole, arsenic trioxide, anastrozole, triptorelin pamoate, ozogamicin, irinotecan hydrochloride, BCG live, leuprolide acetate implant, bexarotene, exemestane, topotecan hydrochloride, gemcitabine HCL, daunorubicin hydrochloride, toremifene citrate, carboplatin, cisplatin, oxaliplatin and any other platinum-containing oncology drug, trastuzumab, lapatinib, gefitinb, cetuximab, panitumumab, temsirolimus, everolimus, vandetanib, vemurafenib, crizotinib, vorinostat, bevacizumab, radiation therapy, hyperthermia, gene therapy and photodynamic therapy.

* * * * *

UNITED STATES PATENT AND TRADEMARK OFFICE
CERTIFICATE OF CORRECTION

PATENT NO.        : 9,452,219 B2
APPLICATION NO.   : 14/122617
DATED             : September 27, 2016
INVENTOR(S)       : Paula J. Bates et al.

It is certified that error appears in the above-identified patent and that said Letters Patent is hereby corrected as shown below:

On the Title Page

(56) References Cited

Page 2, Column 2, Line 26, please delete "PCT/US2009/088491" and insert --PCT/US2008/088491--

Page 3, Column 1, Line 23, please delete "Alvarex" and insert --Alvarez--

Page 3, Column 1, Line 24, please delete "ply" and insert --poly--

Page 6, Column 1, Line 38, please delete "Annuals" and insert --Annals--

Page 6, Column 1, Line 69, please delete "camptothecintreated" and insert --camptothecin-treated--

Page 6, Column 2, Line 47, please delete "aquamous" and insert --squamous--

Page 6, Column 2, Line 60, please delete "multifrug" and insert --multidrug--

Page 7, Column 2, Line 71, please delete "ASP" and insert --ADP--

Page 7, Column 2, Line 73, please delete "oo," and insert --pp.--

Page 8, Column 2, Line 3, please delete "orgin" and insert --origin--

Page 8, Column 2, Line 59, please delete "Rrev" and insert --Rev--

Page 9, Column 1, Line 14, please delete "furing" and insert --during--

Page 9, Column 1, Line 17, please delete "injibit" and insert --inhibit--

Signed and Sealed this
Twenty-sixth Day of June, 2018

Andrei Iancu
*Director of the United States Patent and Trademark Office*

CERTIFICATE OF CORRECTION (continued)
U.S. Pat. No. 9,452,219 B2

Page 9, Column 1, Line 30, please delete "shotfun" and insert --shotgun--

Page 10, Column 1, Line 30, please delete "nanoparticles" and insert --nanoparticle--

Page 11, Column 2, Line 59, please delete "necleolin" and insert --nucleolin--

Page 12, Column 2, Line 10, please insert --15 Pages,-- before Jul. 19, 2016,

Page 12, Column 2, Line 11, please insert --12 Pages,-- before Jul. 21, 2016,

In the Claims

Column 30, Line 59, please delete "mytomycin" and insert --mitomycin--

Column 30, Lines 59-60, please delete "cycly-phosphamide" and insert --cyclophosphamide--

Column 31, Line 2, please delete "gefitinb" and insert --gefitinib--

Column 32, Line 1, please delete "mytomycin" and insert --mitomycin--

Column 32, Lines 1-2, please delete "cycly-phosphamide" and insert --cyclophosphamide--

Column 32, Line 11, please delete "gefitinb" and insert --gefitinib--

Column 32, Line 20, please delete "mytomycin" and insert --mitomycin--

Column 32, Lines 20-21, please delete "cycly-phosphamide" and insert --cyclophosphamide--

Column 32, Line 30, please delete "gefitinb" and insert --gefitinib--

SEQUENCE LISTING

```
<160> NUMBER OF SEQ ID NOS: 38

<210> SEQ ID NO 1
<211> LENGTH: 29
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 1
tttggtggtg gtggttgtgg tggtggtgg                                           29

<210> SEQ ID NO 2
<211> LENGTH: 29
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 2
tttggtggtg gtggttttgg tggtggtgg                                           29

<210> SEQ ID NO 3
<211> LENGTH: 29
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 3
tttggtggtg gtggtggtgg tggtggtgg                                           29

<210> SEQ ID NO 4
<211> LENGTH: 29
<212> TYPE: DNA
<213> ORGANISM: Artificial Sequence
```

```
<220> FEATURE:
<223> OTHER INFORMATION: Description of Artificial Sequence: Synthetic
      polynucleotide sequence

<400> SEQUENCE: 4
tttggtggtg gtggtttggg tggtggtgg                                         29

<210> SEQ ID NO 5
<211> LENGTH: 13
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 5
tggtggtggt ggt                                                          13

<210> SEQ ID NO 6
<211> LENGTH: 14
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 6
ggtggttgtg gtgg                                                         14

<210> SEQ ID NO 7
<211> LENGTH: 15
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 7
gttgtttggg gtggt                                                        15

<210> SEQ ID NO 8
<211> LENGTH: 15
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 8
ttgggggggg tgggt                                                        15

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 9
ggttggggtg ggtggggtgg gtggg                                             25

<210> SEQ ID NO 10
<211> LENGTH: 26
<212> TYPE: DNA
<213> ORGANISM: Artificial Sequence
<220> FEATURE:
```

```
<223> OTHER INFORMATION: Description of Artificial Sequence: Synthetic
      polynucleotide sequence

<400> SEQUENCE: 10
ggtggtggtg gttgtggtgg tggtgg                                              26

<210> SEQ ID NO 11
<211> LENGTH: 28
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 11
tttggtggtg gtggttgtgg tggtggtg                                            28

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 12
tttggtggtg gtggtgtggt ggtggtgg                                            28

<210> SEQ ID NO 13
<211> LENGTH: 29
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 13
ggtggtggtg gttgtggtgg tggtggttt                                           29

<210> SEQ ID NO 14
<211> LENGTH: 32
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 14
ggtggttgtg gtggttgtgg tggttgtggt gg                                       32

<210> SEQ ID NO 15
<211> LENGTH: 32
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 15
tttggtggtg gtggttgtgg tggtggtggt tt                                       32

<210> SEQ ID NO 16
<211> LENGTH: 56
<212> TYPE: DNA
<213> ORGANISM: Artificial Sequence
<220> FEATURE:
<223> OTHER INFORMATION: Description of Artificial Sequence: Synthetic
``` polynucleotide sequence

<400> SEQUENCE: 16
ggtggtggtg gttgtggtgg tggtggttgt ggtggtggtg gttgtggtgg tggtgg        56

<210> SEQ ID NO 17
<211> LENGTH: 35
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 17
tcgagaaaaa ctctcctctc cttccttcct ctcca                                35

<210> SEQ ID NO 18
<211> LENGTH: 29
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 18
tttcctcctc ctccttctcc tcctcctcc                                       29

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 19
ttagggttag ggttagggtt aggg                                            24

<210> SEQ ID NO 20
<211> LENGTH: 11
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 20
ggtggtggtg g                                                          11

<210> SEQ ID NO 21
<211> LENGTH: 14
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 21
ggtggttgtg gtgg                                                       14

<210> SEQ ID NO 22
<211> LENGTH: 15
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 22
ggttggtgtg gttgg                                                     15

<210> SEQ ID NO 23
<211> LENGTH: 10
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 23
gggttttggg                                                           10

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 24
ggttttggtt ttggttttgg                                                20

<210> SEQ ID NO 25
<211> LENGTH: 15
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 25
ggttggtgtg gttgg                                                     15

<210> SEQ ID NO 26
<211> LENGTH: 12
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 26
ggggttttgg gg                                                        12

<210> SEQ ID NO 27
<211> LENGTH: 10
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 27
gggttttggg                                                           10

<210> SEQ ID NO 28
<211> LENGTH: 28
<212> TYPE: DNA
<213> ORGANISM: Artificial Sequence
<220> FEATURE:
<223> OTHER INFORMATION: Description of Artificial Sequence: Synthetic
      polynucleotide sequence

```
<400> SEQUENCE: 28
ggggttttgg ggttttgggg ttttgggg                                         28

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 29
ttggggttgg ggttggggtt gggg                                             24

<210> SEQ ID NO 30
<211> LENGTH: 16
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 30
gggtgggtgg gtgggt                                                      16

<210> SEQ ID NO 31
<211> LENGTH: 26
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 31
ggttttggtt ttggttttgg ttttgg                                           26

<210> SEQ ID NO 32
<211> LENGTH: 29
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 32
tttcctcctc ctccttctcc tcctcctcc                                        29

<210> SEQ ID NO 33
<211> LENGTH: 26
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 33
cctcctcctc cttctcctcc tcctcc                                           26

<210> SEQ ID NO 34
<211> LENGTH: 6
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 34
```

```
tggggt                                                                  6

<210> SEQ ID NO 35
<211> LENGTH: 7
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 35 gcatgct                                                                 7

<210> SEQ ID NO 36
<211> LENGTH: 11
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 36
gcggtttgcg g                                                           11

<210> SEQ ID NO 37
<211> LENGTH: 4
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 37 tagg                                                                    4

<210> SEQ ID NO 38
<211> LENGTH: 23
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 38
ggggttgggg tgtggggttg ggg                                              23
```